US011241519B2

(12) United States Patent
Laudenslager et al.

(10) Patent No.: US 11,241,519 B2
(45) Date of Patent: Feb. 8, 2022

(54) SMALL FLEXIBLE LIQUID CORE CATHETER FOR LASER ABLATION IN BODY LUMENS AND METHODS FOR USE

(71) Applicant: RA MEDICAL SYSTEMS, INC., Carlsbad, CA (US)

(72) Inventors: James B. Laudenslager, San Marcos, CA (US); Dean S. Irwin, Carlsbad, CA (US)

(73) Assignee: RA MEDICAL SYSIEMS, INC., Carlsbad, CA (US)

( * ) Notice: Subject to any disclaimer, the term of this patent is extended or adjusted under 35 U.S.C. 154(b) by 129 days.

(21) Appl. No.: 16/549,516

(22) Filed: Aug. 23, 2019

(65) Prior Publication Data
US 2019/0374684 A1 Dec. 12, 2019

Related U.S. Application Data

(60) Continuation of application No. 15/615,734, filed on Jun. 6, 2017, now Pat. No. 11,123,458, which is a
(Continued)

(51) Int. Cl.
*A61L 29/04* (2006.01)
*A61B 18/24* (2006.01)
*A61L 29/08* (2006.01)
*A61L 29/14* (2006.01)
*A61B 18/20* (2006.01)
(Continued)

(52) U.S. Cl.
CPC ............ *A61L 29/041* (2013.01); *A61B 18/24* (2013.01); *A61B 18/245* (2013.01); *A61L 29/08* (2013.01); *A61L 29/085* (2013.01); *A61L 29/14* (2013.01); *A61B 2018/206* (2013.01); *A61B 2018/2025* (2013.01); *A61B 2090/3966* (2016.02); *A61M 25/0009* (2013.01)

(58) Field of Classification Search
CPC ...... A61L 29/041; A61L 29/08; A61L 29/085; A61L 29/14; A61B 18/24; A61B 18/245; A61B 2090/3966; A61B 2018/2025; A61B 2018/206; A61M 25/0009
USPC .......................................................... 606/7
See application file for complete search history.

(56) References Cited

U.S. PATENT DOCUMENTS

| 3,740,113 A | 6/1973 | Cass |
| 3,995,934 A | 12/1976 | Nath |

(Continued)

FOREIGN PATENT DOCUMENTS

| CN | 1652722 A | 8/2005 |
| CN | 1832708 A | 9/2006 |

(Continued)

OTHER PUBLICATIONS

Notice of Allowance dated Oct. 17, 2019 in U.S. Appl. No. 15/359,412, filed Nov. 22, 2016, published as: 2017/0143424 on May 25, 2017.
(Continued)

*Primary Examiner* — Aaron F Roane
(74) *Attorney, Agent, or Firm* — Schmeiser, Olsen & Watts LLP

(57) ABSTRACT

Embodiments relate to the design and use of a low profile ablation catheter with a liquid core for use in laser ablation removal of arterial plaque blockages to restore blood flow.

14 Claims, 25 Drawing Sheets

Related U.S. Application Data division of application No. 13/651,070, filed on Oct. 12, 2012, now Pat. No. 9,700,655.

(60) Provisional application No. 61/547,435, filed on Oct. 14, 2011.

(51) Int. Cl.
  *A61B 90/00*  (2016.01)
  *A61M 25/00*  (2006.01)

(56) References Cited

U.S. PATENT DOCUMENTS

| | | |
|---|---|---|
| 4,009,382 A | 2/1977 | Nath |
| 4,045,119 A | 8/1977 | Eastgate |
| 4,380,460 A | 4/1983 | Otstot et al. |
| 4,516,972 A | 5/1985 | Samson et al. |
| 4,530,569 A | 7/1985 | Squire |
| 4,641,912 A | 2/1987 | Goldenberg |
| 4,686,979 A | 8/1987 | Gruen et al. |
| 4,720,166 A | 1/1988 | Ohmori et al. |
| 4,732,448 A | 3/1988 | Goldenberg |
| 4,739,768 A | 4/1988 | Engleson |
| 4,747,405 A | 5/1988 | Leckrone |
| 4,747,662 A | 5/1988 | Fitz |
| 4,762,129 A | 8/1988 | Bonzel |
| 4,770,653 A | 9/1988 | Shturman |
| 4,784,132 A | 11/1988 | Fox et al. |
| 4,784,135 A | 11/1988 | Blum et al. |
| 4,793,359 A | 12/1988 | Sharrow |
| 4,799,754 A | 1/1989 | Goldenberg |
| 4,800,876 A | 1/1989 | Fox et al. |
| 4,834,093 A | 5/1989 | Littleford et al. |
| 4,844,062 A | 7/1989 | Wells |
| 4,848,336 A | 7/1989 | Fox et al. |
| 4,850,351 A | 7/1989 | Herman et al. |
| 4,862,886 A | 9/1989 | Clarke et al. |
| 4,907,133 A | 3/1990 | Nath |
| 4,913,142 A | 4/1990 | Kittrell et al. |
| 4,919,508 A | 4/1990 | Grace et al. |
| 4,927,231 A | 5/1990 | Levatter |
| 4,930,863 A | 6/1990 | Croitoriu et al. |
| 4,998,794 A | 3/1991 | Holzman |
| 5,005,944 A | 4/1991 | Laakmann et al. |
| 5,037,404 A | 8/1991 | Gold et al. |
| 5,040,548 A | 8/1991 | Yock |
| 5,041,108 A | 8/1991 | Fox et al. |
| 5,061,273 A | 10/1991 | Yock |
| 5,076,659 A | 12/1991 | Bekiarian et al. |
| 5,100,388 A | 3/1992 | Behl et al. |
| 5,157,750 A | 10/1992 | Grace et al. |
| 5,165,773 A | 11/1992 | Nath |
| 5,176,674 A | 1/1993 | Hofmann |
| 5,188,632 A | 2/1993 | Goldenberg |
| 5,263,952 A | 11/1993 | Grace et al. |
| 5,267,341 A | 11/1993 | Shearin |
| 5,267,993 A | 12/1993 | Grace et al. |
| 5,290,277 A | 3/1994 | Vercimak et al. |
| 5,304,171 A | 4/1994 | Gregory et al. |
| 5,321,783 A | 6/1994 | Nielson et al. |
| 5,350,395 A | 9/1994 | Yock |
| 5,395,361 A | 3/1995 | Fox et al. |
| 5,412,750 A | 5/1995 | Nath |
| 5,419,760 A | 5/1995 | Narcisco, Jr. |
| 5,429,604 A | 7/1995 | Hammersmark et al. |
| 5,429,617 A | 7/1995 | Hammersmark et al. |
| 5,438,873 A | 8/1995 | Wlodarczyk et al. |
| 5,456,680 A | 10/1995 | Taylor et al. |
| 5,484,433 A | 1/1996 | Taylor et al. |
| 5,497,441 A | 3/1996 | Croitoru et al. |
| 5,514,128 A | 5/1996 | Hillsman et al. |
| 5,573,531 A | 11/1996 | Gregory |
| 5,584,558 A | 12/1996 | Nath |
| 5,675,689 A | 10/1997 | Nath |
| 5,722,972 A | 3/1998 | Power |
| 5,737,473 A | 4/1998 | Nath |
| 5,836,940 A | 11/1998 | Gregory |
| 5,857,052 A | 1/1999 | Nath |
| 5,868,665 A | 2/1999 | Biggs |
| 5,976,093 A | 11/1999 | Jang |
| 5,989,243 A | 11/1999 | Goldenberg |
| 6,022,309 A | 2/2000 | Celliers et al. |
| 6,106,510 A | 8/2000 | Lunn et al. |
| 6,117,128 A | 9/2000 | Gregory |
| 6,143,013 A | 11/2000 | Samson et al. |
| 6,163,641 A | 12/2000 | Eastgate |
| 6,165,163 A | 12/2000 | Chien et al. |
| 6,212,422 B1 | 4/2001 | Berg et al. |
| 6,263,236 B1 | 7/2001 | Kasinkas et al. |
| 6,306,124 B1 | 10/2001 | Jones et al. |
| 6,314,226 B1 | 11/2001 | Nath |
| 6,314,227 B1 | 11/2001 | Nath |
| 6,368,318 B1 | 4/2002 | Visuri et al. |
| 6,418,257 B1 | 7/2002 | Nath |
| 6,507,688 B1 | 1/2003 | Nath |
| 6,520,934 B1 | 2/2003 | Lee et al. |
| 6,571,049 B1 | 5/2003 | Nath |
| 6,585,760 B1 | 7/2003 | Fogarty |
| 6,609,014 B1 | 8/2003 | Allison et al. |
| 6,824,553 B1 | 11/2004 | Samson et al. |
| 6,893,427 B1 | 5/2005 | Jimenez |
| 6,963,688 B2 | 11/2005 | Nath |
| 6,974,473 B2 | 12/2005 | Barclay et al. |
| 7,050,692 B2 | 5/2006 | Harlen et al. |
| 7,144,248 B2 | 12/2006 | Irwin |
| 7,144,381 B2 | 12/2006 | Gertner |
| 7,167,622 B2 | 1/2007 | Temelkuran et al. |
| 7,402,151 B2 | 7/2008 | Rosenman et al. |
| 7,572,254 B2 | 8/2009 | Hebert et al. |
| 7,762,980 B2 | 7/2010 | Gertner |
| 8,152,795 B2 | 4/2012 | Farr et al. |
| 8,231,551 B2 | 7/2012 | Griffin et al. |
| 8,652,084 B2 | 2/2014 | Akingba |
| 9,339,628 B2 | 5/2016 | Adams et al. |
| 9,962,527 B2 | 5/2018 | Laudenslager et al. |
| 10,384,038 B2 | 8/2019 | Laudensalger et al. |
| 10,478,251 B2 | 11/2019 | Shuffler et al. |
| 10,485,613 B2 | 11/2019 | Hendrick et al. |
| 10,492,876 B2 | 12/2019 | Anastassiou et al. |
| 10,555,772 B2 | 2/2020 | Laudenslger et al. |
| 10,799,671 B2 | 10/2020 | Shimada et al. |
| 2003/0023236 A1 | 1/2003 | Gowda et al. |
| 2003/0078569 A1 | 4/2003 | Caldera et al. |
| 2004/0220473 A1 | 11/2004 | Lauldi |
| 2005/0031281 A1 | 2/2005 | Nath |
| 2005/0254237 A1 | 11/2005 | Nath et al. |
| 2006/0271090 A1 | 11/2006 | Shaked et al. |
| 2007/0244495 A1 | 10/2007 | Kwon |
| 2007/0250105 A1* | 10/2007 | Ressemann ...... A61B 17/12104 606/196 |
| 2008/0188793 A1 | 8/2008 | Kozak et al. |
| 2008/0249515 A1 | 10/2008 | Taylor |
| 2008/0317991 A1* | 12/2008 | Pieslak ................. A61L 29/041 428/36.91 |
| 2009/0112198 A1 | 4/2009 | Khanna et al. |
| 2009/0163899 A1 | 6/2009 | Burton et al. |
| 2009/0227997 A1* | 9/2009 | Wang .................... A61B 18/24 606/10 |
| 2009/0254074 A1 | 10/2009 | Splinter et al. |
| 2009/0264898 A1 | 10/2009 | Miller et al. |
| 2010/0004607 A1* | 1/2010 | Wilson .................. A61B 17/22 604/266 |
| 2010/0016842 A1 | 1/2010 | Fix |
| 2010/0087783 A1 | 4/2010 | Weber et al. |
| 2010/0114081 A1 | 5/2010 | Keeler et al. |
| 2010/0152720 A1 | 6/2010 | Sauro et al. |
| 2010/0198193 A1 | 8/2010 | Trapp |
| 2011/0238041 A1 | 9/2011 | Lim et al. |
| 2012/0277671 A1 | 11/2012 | Fuentes |
| 2013/0096545 A1 | 4/2013 | Laudenslager et al. |
| 2015/0057639 A1 | 2/2015 | Storbeck et al. |
| 2015/0105714 A1 | 4/2015 | Laudenslager et al. |
| 2017/0143424 A1 | 5/2017 | Laudenslager et al. |
| 2017/0266351 A1 | 9/2017 | Laudenslager et al. |

(56) References Cited

U.S. PATENT DOCUMENTS

| | | |
|---|---|---|
| 2018/0008348 A1 | 1/2018 | Grace et al. |
| 2018/0021550 A1 | 1/2018 | Laudenslager et al. |
| 2018/0021551 A1 | 1/2018 | Laudenslager et al. |
| 2018/0021552 A1 | 1/2018 | Laudenslager et al. |
| 2018/0250498 A1 | 9/2018 | Stern et al. |
| 2019/0142517 A1 | 5/2019 | Chia et al. |
| 2019/0160259 A1 | 5/2019 | Cottone et al. |
| 2019/0290356 A1 | 9/2019 | Wood et al. |
| 2019/0366036 A1 | 12/2019 | Jalgaonkar et al. |
| 2020/0046429 A1 | 2/2020 | Tschida et al. |
| 2020/0230294 A1 | 7/2020 | Laudenslager et al. |
| 2020/0261154 A1 | 8/2020 | Ogata et al. |

FOREIGN PATENT DOCUMENTS

| | | |
|---|---|---|
| EP | 0247746 | 12/1987 |
| EP | 0368512 | 5/1990 |
| EP | 0590268 | 4/1994 |
| EP | 0727054 | 8/1996 |
| EP | 1757428 | 2/2007 |
| EP | 2301617 | 3/2011 |
| WO | WO 95/012138 | 5/1995 |
| WO | WO 97/039691 | 10/1997 |
| WO | WO 98/038538 | 9/1998 |
| WO | WO 00/030696 | 6/2000 |
| WO | WO 09/120871 | 10/2009 |

OTHER PUBLICATIONS

Non-Final Office Action dated Aug. 5, 2019 in U.S. Appl. No. 15/359,412, filed Nov. 22, 2016, published as: 2017/0143424 on May 25, 2017.

"Prevalence and Cost of ESRD Therapy," USRDS Annual Data Report 1991, American Journal of Kidney Diseases, vol. 18, No. 5, Suppl 2, Nov. 1991; pp. 21-29.

Bittl; Catheter Interventions for Hemodiaylysis Fistulas and Grafts: J Am Coll Cardiol Intv vol. 3 pp. 1-11 (2010).

Das, "Excimer Laser-Assisted Angioplasty for Infrainguinal Artery Disease" J of Endovasc Therapy vol. 16 pp. 1198-11104(2009).

Drooz, "Ultrahigh-pressure angioplasty of a transposed brachiocephalic fistula with recurrent stenosis," ConQuest PTA Dilation Catheter, Bard Peripheral Vascular, Inova Fairfax Hospital; Fairfax, VA, Aug. 2005.

Forauer, Hoffer, et al.; "Dialysis Access Venous Stenoses: Treatment with Balloon Angioplasty-1—versus 3-minute Inflation Times" Radiology vol. 249, pp. 375-381 (2008).

Gandini and Del Giudice; "Use of laser Atherectomy with drug-eluting balloon angioplasty shows benefit in treatment of in-stent restenosis" presented at EuroPCR 2014 Congress (May 20-23, 2014), Paris, France.

Haage, Verwerk et al.: "Percutaneous treatment of thrombosed primary arteriovenous hemodialysis access fistulae" Kidney International, vol. 57, pp. 1169-1175(2000).

Hamburger et al., New Aspects of Excimer Laser Coronary Angioplasty Physical Aspects and Clinical Results, printed by Optima Grafische Communicatie ISBN 90-73235-27-8, Rotterdam, Jaap N. Hamburger, Dec. 1998.

Hofstra et al., "Enhanced Cellular Proliferation in Intact Stenotic Lesions Derived From Human Arteriovenous Fistulas and peripheral Bypass Grafts. Does it correlate with Flow Parameters?" Circulation, 1996;94:1283-1290.

Janis et al. "Laser Thrombolysis in an in vitro Model" Lasers in Surg.: Advanced Characterization, Therapeutics and Systems, Pro. of SPIE vol. 3907 pp. 582-585 (2000).

Ma et al., "Interaction of excimer laser with blood components and thrombosis" Life Science J. vol. 5 pp. 19-26 (2008).

Mickley; "Stenosis and thrombus in hemodialysis fistulae and grafts: the surgeon's point of view" Nephrol Dial Transplant vol. 19 pp. 309-311 (2004).

Miller and Friedman, "Balloon-Assisted Maturation of Arteriovenous Fistulas" Endovascular Today Endovascular Today, pp. 46-54 (2010).

Morph® "Universal Deflectable Guide Catheter," BioCardia® Cat # 01037-5.

Mysliwiec, "Vascular access thrombosis-what are the possibilities of intervention?" Nephrol Dial Transplant (1997) 12: Editorial Comments.

Ozkan, Gungor et al. "Endovascular Stent Placement of Juxtaanastomotic Stenosis in Native Arteriovenus Fistula After Unsuccessful Balloon Angioplasty" Iranian J of Radiology, vol. 10 pp. 133-139 (2013).

Papaioannou et al. "Excimer Laser Assisted Thrombolysis: The Effect of Fluence, Repetition Rate and Catheter Size" Proc. SPIE 4609, Lasers in Surgery; Advanced Characterization, Therapeutics and Systems XII 413 (2002).

Papaioannou et al. "Particulate debris analysis during excimer laser thrombolysis: An in-vitro study" Proc. SPIE 4609, Lasers in Surgery; Advanced Characterization, Therapeutics and Systems XII 404 (2002).

Shenoy, "Surgical anatomy of upper arm: what is needed for AVF planning" J of Vascul Access vol. 10 pp. 223-232(2009).

Sofocleous et al.; "Dialysis Fistulas" In Medscape (2013).

Staniloae et al., "Obrital Atherectomy: Device Evolution and Clinical Data" Periperal Vase. Disease, vol. 26, pp. 215-219 (2014).

Van den Berg, Pedrotti et al.; "In-Stent Restenosis: Mid-Term Results of Debulking Using Excimer Laser and Drug-Eluting Balloons: Sustained Benefit?" J Invasive Cardiol vol. 26 pp. 333-337(2014).

Van den Berg; "Atherectomy and DCB in the SFA: A Summary of the Data" Endovascular Today pp. 28-32(2014).

Walker et al., "Excimer Laser-Assisted Angioplasty" Endovasc. Today,pp. 75-76 (2007).

Zaleski; "Declotting, Maintenance, and Avoiding Procedural Complications of Native Arteriovenous Fistulae" Semin Intervent Radiol. vol. 21, pp. 83-93 (2004).

Zwaan et al., "Initial clinical experience with a new pulsed dye laser device in angioplasty of limb ischemia and shunt fistula obstructions," European Journal of Radiology, 14 (1992) pp. 72-76.

Extended European Search Report dated May 29, 2015 in European Patent Application No. EP 12840010.8, filed: Oct. 12, 2012.

International Preliminary Report on Patentability dated Apr. 24, 2014 in International Application No. PCT/US2012/060065 filed Oct. 12, 2012.

International Search Report and Written Opinion dated Mar. 29, 2013 in International Application No. PCT/US2012/060065 filed Oct. 12, 2012.

Notice of Allowance dated Jan. 30, 2018 in U.S. Appl. No. 14/515,435, filed Oct. 15, 2014, published as: 2015/0105714 on Apr. 16, 2015 and issued as: U.S. Pat. No. 9,962,527 on May 8, 2018.

ExParte Quayle Action dated Dec. 12, 2017 in U.S. Appl. No. 14/515,435, filed Oct. 15, 2014, published as: 2015/0105714 on Apr. 16, 2015 and issued as: U.S. Pat. No. 9,962,527 on May 8, 2018.

Notice of Allowance dated Apr. 19, 2019 in U.S. Appl. No. 15/723,062, filed Oct. 2, 2017, published as: 2018/0021551 on Jan. 25, 2018.

Non Final Office Action dated Dec. 31, 2018 in U.S. Appl. No. 15/723,062, filed Oct. 2, 2017, published as: 2018/0021551 on Jan. 25, 2018.

Non Final Office Action dated Nov. 30, 2018 in U.S. Appl. No. 15/723,057, filed Oct. 2, 2017, published as: 2018/0021550 on Jan. 25, 2018 and issued as: U.S. Pat. No. 10,245,417 on Apr. 2, 2019.

Notice of Allowance dated Dec. 31, 2018 in U.S. Appl. No. 15/723,057, filed Oct. 2, 2017, published as: 2018/0021550 on Jan. 25, 2018 and issued as: U.S. Pat. No. 10,245,417 on Apr. 2, 2019.

Notice of Allowance dated Feb. 26, 2019 in U.S. Appl. No. 15/723,057, filed Oct. 2, 2017, published as: 2018/0021550 on Jan. 25, 2018 and issued as: U.S. Pat. No. 10,245,417 on Apr. 2, 2019.

Notice of Allowance dated Apr. 17, 2019 in U.S. Appl. No. 15/723,067, filed Oct. 2, 2017, published as: 2018/0021552 on Jan. 25, 2018.

(56) References Cited

OTHER PUBLICATIONS

Notice of Allowance dated Feb. 27, 2019 in U.S. Appl. No. 15/723,067, filed Oct. 2, 2017, published as: 2018/0021552 on Jan. 25, 2018.
ExParte Quayle Action dated Nov. 29, 2018 in U.S. Appl. No. 15/723,067, filed Oct. 2, 2017, published as: 2018/0021552 on Jan. 25, 2018.
Notice of Allowance dated Apr. 20, 2017 in U.S. Appl. No. 13/651,070, filed Oct. 12, 2012 and published as: US-2013/0096545 on: Apr. 18, 2013 and issued as: U.S. Pat. No. 9,700,655 on Jul. 11, 2017.
Final Office Action dated Sep. 15, 2016 in U.S. Appl. No. 13/651,070, filed Oct. 12, 2012 and published as: US-2013/0096545 on: Apr. 18, 2013 and issued as: U.S. Pat. No. 9,700,655 on Jul. 11, 2017.
Non-Final Office Action dated Feb. 12, 2016 in U.S. Appl. No. 13/651,070, filed Oct. 12, 2012 and published as: US-2013/0096545 on: Apr. 18, 2013 and issued as: U.S. Pat. No. 9,700,655 on Jul. 11, 2017.
Extended European Search Report dated Aug. 13, 2019 in European Patent Application No. EP 19163464.1, filed: Mar. 18, 2019.
Non-Final Office Action dated Sep. 9, 2020 in U.S. Appl. No. 15/615,734, filed Jun. 6, 2017 and published as: US-2017/0266351 on: Sep. 21, 2017.
Non-Final Office Action dated Sep. 30, 2020 in U.S. Appl. No. 16/502,766, filed Jul. 3, 2019 and published as: US-2019/0336732 on: Nov. 7, 2019.
International Search Report and Written Opinion dated Jul. 12, 2021 in International Patent Application: PCT/US21/19199 filed Feb. 23, 2021.
Non-Final Office Action dated Jan. 12, 2021 in U.S. Appl. No. 16/359,889, filed Mar. 20, 2019 and published as: US-2019/0290356 on: Sep. 26, 2019.
Notice of Allowance dated May 10, 2021 in U.S. Appl. No. 15/615,734, filed Jun. 6, 2017 and published as: 2017/0266351 on: Sep. 21, 2017.
Non-Final Office Action dated Oct. 13, 2021 in U.S. Appl. No. 16/843,736, filed Apr. 8, 2020 and published as: 2020/0230294 on Jul. 23, 2020.

* cited by examiner

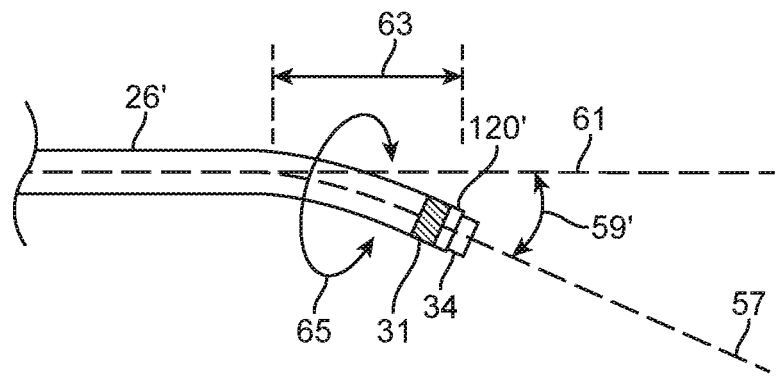
FIG. 22
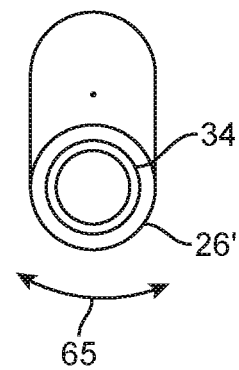
FIG. 23
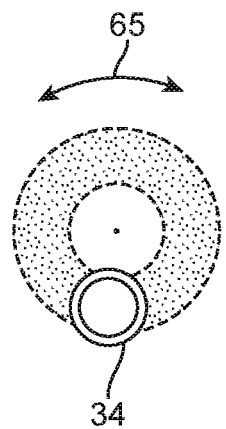   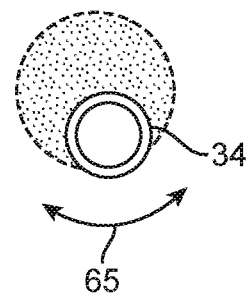
FIG. 24   FIG. 25

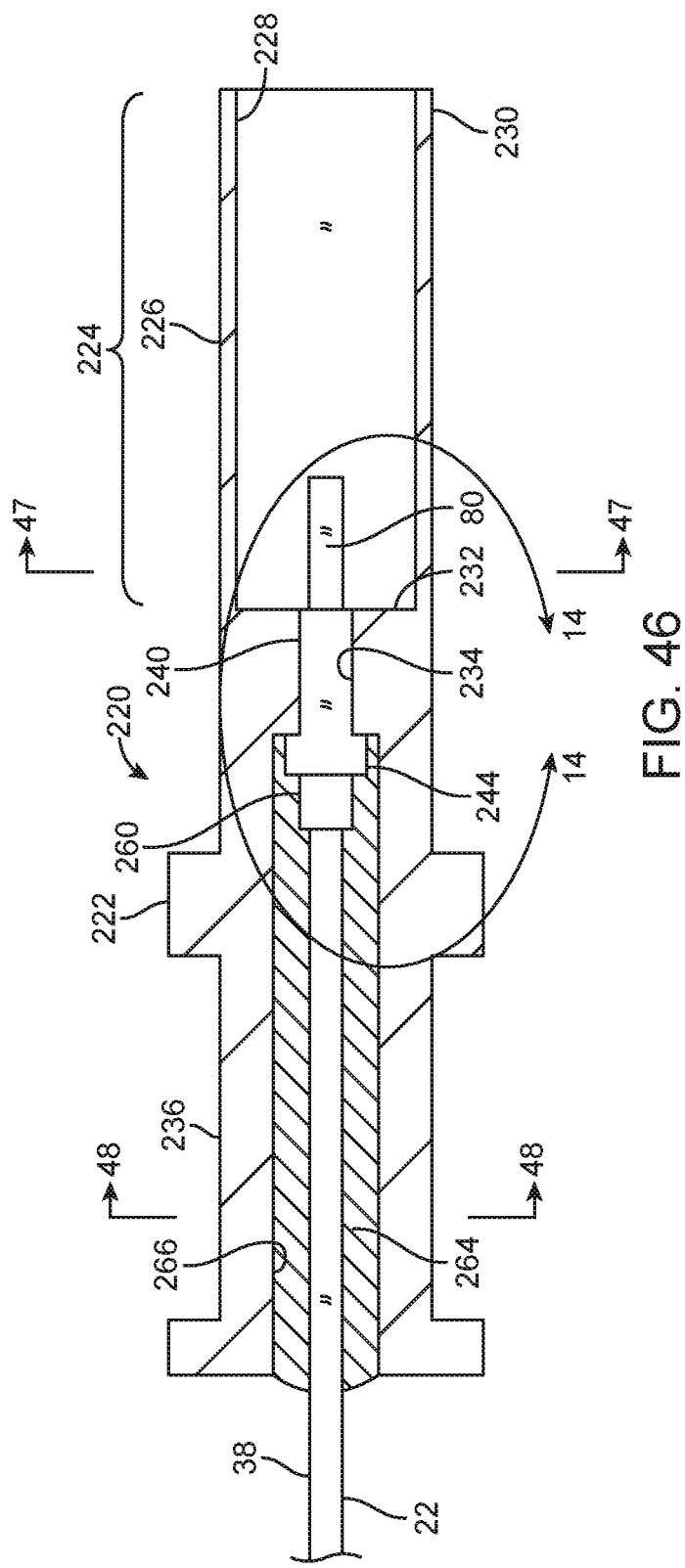

SMALL FLEXIBLE LIQUID CORE CATHETER FOR LASER ABLATION IN BODY LUMENS AND METHODS FOR USE

RELATED APPLICATIONS

This application is a continuation of copending U.S. patent application Ser. No. 15/615,734, filed Jun. 6, 2017, entitled Small Flexible Liquid Core Catheter for Laser Ablation in Body Lumens and Methods for Use, by J. Laudenslager et al., which is a divisional application of U.S. patent application Ser. No. 13/651,070, filed Oct. 12, 2012, entitled Small Flexible Liquid Core Catheter for Laser Ablation in Body Lumens and Methods for Use, by J. Laudenslager et al., which claims priority under 35 USC 119(e) from U.S. Provisional Patent Application No. 61/547,435, filed Oct. 14, 2011, entitled Small Flexible Liquid Core Catheter for Laser Ablation and Method for Use, by J. Laudenslager et al., each of which is incorporated by reference herein in its entirety.

BACKGROUND

Laser catheters and laser delivery systems in general have wide range of applications in the medical field. Such systems may be used to deliver laser energy to desired sites of a patient's anatomy, and may be particularly suitable for delivering laser energy to locations within a patient's body that allow for minimally invasive treatment of a variety of indications using a variety of treatment modalities. Examples of some laser treatment modalities include heating tissue, stimulating tissue, drug activation within a patient's tissue and ablation of tissue.

Laser catheters currently approved for clearing blockages in human arteries may use single or more commonly multiple bundle pure silica optical fibers for indications using ultraviolet laser pulse durations greater than about 50 nsec, usually greater than about 100 nsec to prevent damage to small diameter optical fibers used in multiple optical fiber delivery catheter designs. Typically, optical fiber elements having a transmissive core with a transverse dimension or diameter of about 50 microns to about 100 microns may be used in ablation catheters having multiple optical fiber bundles.

In some cases, single large diameter optical fibers having a transmissive core with a transverse dimension or diameter greater than about 130 microns may be too stiff or resistant to longitudinal bending for use in the arteries of a patient, particularly the coronary arteries of a human patient. Therefore, multiple optical fiber bundles using optical fibers having a smaller transverse dimension or diameter may be used to improve flexibility of the catheter while maintaining a constant transmissive core area. These optical fiber laser catheters may be up to 12 feet long and contain from about 50 optical fibers to about 300 optical fibers depending on the cross sectional size of the catheter ablation tip. These pure silica optical fibers are expensive and have a low percentage of cutting area due to the clad and buffer used on the outside of the light conducting or transmissive core as well as a low density packing factor for the multiple fibers having a circular transverse cross section disposed in a bundle.

Another way for delivering laser energy to a remote site includes the use of a fluid core waveguide. Existing commercial fluid core waveguides having a transmissive fluid core may typically have an inner diameter of about 2 mm to about 5 mm and a length of about 1 m to about 5 m and have useful light transmission from the ultraviolet to the visible wavelengths at greater than 50% transmission in some cases. Such designs may be robust for repeated use but are large in size and may not be scalable to a smaller more flexible design for use as a disposable catheter in tortuous vessels such as a patient's vasculature. Such designs may also not be adaptable to smaller more flexible embodiments to be used with a high pulse power and high pulse energy laser such as the ultraviolet excimer laser, particularly the 308 nm XeCl excimer. Also, many of the previously disclosed fluids used for the transmissive core of these fluid core waveguides may not be suitably biocompatible for use inside the human body.

What has been needed is a fluid core waveguide based ablation catheter that is small and flexible enough to navigate a patient's vasculature, uses biocompatible fluids, and is economical to manufacture. What has also been needed is a fluid core waveguide based ablation catheter that can be efficiently packaged and sterilized and maintain clinical integrity during a useful shelf life after shipment to an end user.

SUMMARY

Some embodiments of a laser catheter system to ablate blockages in body lumens using high energy and high power short duration laser pulses may include a high energy, high power short duration ultraviolet pulsed laser source. Such systems may also include a low profile, kink resistant, torqueable liquid core ablation catheter operatively coupled to the laser source. In some cases, the liquid core ablation catheter may have an elongate multi-layer catheter tube including a thin inner luminal layer of a low index of refraction (IR), U.V. transparent, amorphous fluoropolymer having an index of refraction of less than or equal to about 1.33 disposed on an inside surface of the base tubular layer; an ultraviolet grade output optical window or window assembly sealed to a distal end of the catheter tube; an ultraviolet grade input optical window sealed to a proximal end of the catheter tube to create a fluid tight core liquid volume; and a biocompatible U.V. transparent fluid disposed within and completely filling the core liquid volume formed between an inner surface of the thin inner luminal layer, the output optical window and the input optical window.

Some embodiments of a laser system to ablate blockages in body lumens using high energy and high power short duration laser pulses include a high energy, high power short duration ultraviolet pulsed laser source. The system may also include a low profile, kink resistant, torqueable liquid core ablation catheter operatively coupled to the laser source. Such a liquid core ablation catheter may include an elongate multi-layer catheter tube, which has a base tubular layer including fluorinated or mostly fluorinated material, a braided layer disposed over an outside surface of the base tubular layer, an over-jacket layer coated over the braided layer and base tubular layer to encapsulate the braided layer, and a thin inner luminal layer of a low index of refraction (IR), U.V. transparent, amorphous fluoropolymer having an index of refraction of less than or equal to about 1.33 disposed on an inside surface of the base tubular layer that may be made by drip coating a solution of amorphous fluoropolymer to the inside surface and drying off the solvent. The liquid core ablation catheter may also include an ultraviolet grade output optical window sealed to a lumenal surface, such as an inner lumenal surface of the catheter tube, wherein an area ratio of the output optical window to a total area of an outer diameter of the catheter tube, and in particular, the catheter tube distal tip, may be greater than about 40%. The catheter may further include an ultraviolet grade input optical window sealed to a surface of the catheter tube, such as an inner lumenal surface or outer surface of the catheter tube at a proximal end of the catheter tube to create a fluid tight core liquid volume. A biocompatible U.V. transparent fluid may be disposed within and completely filling a core liquid volume formed between an inner surface of the thin inner luminal layer, a proximal surface of the output optical window and a distal surface of the output optical window.

Some embodiments of a support catheter for use supporting a liquid core ablation catheter may include an inner tubular layer that may be less than about 0.001 inches in thickness, a thin over layer with of a material with a higher durometer than the inner tubular layer, a braided layer disposed over an outer surface of the inner tubular layer, and an outer layer covering the braided layer. In some cases, the support catheter may also have a wall thickness of less than about 0.006 inches. For some such embodiments, the support catheter may include an inner lumen with an inner diameter which is configured to accommodate passage of a liquid core ablation catheter and space therebetween sufficient for saline injection to flush blood and contrast fluid in front of the ablation catheter distal end. For some embodiments, the inner tubular layer of this catheter may include a low friction material to ease passage of the ablation catheter and may also include the requisite torqueability, pushability and kink resistance to guide an ablation catheter with a low enough profile to advance through an opening generated by such laser ablation of tissue with the ablation catheter. Some support catheter embodiments may include a multi-lumen support catheter, having one or more guidewire lumens, such as 2, 3, 4 or more guidewire lumens, and a working lumen configured for passage of an ablation catheter.

Some methods of ablation of blockages in a lumen of a human vessel may include positioning a support catheter at a target site of a blockage of the vessel, inserting a liquid core ablation catheter adjacent the blockage, injecting saline through an inner lumen of the support catheter to flush contrast fluid and blood from a distal tip of the liquid core ablation catheter, emitting ablative laser energy from a distal end of the ablation catheter and advancing the liquid core ablation catheter about 4 mm to about 6 mm from a distal end of the support catheter while lasing. In some cases, the ablation catheter may be advanced about 5 mm from a distal end of the support catheter. Thereafter, the support catheter may be repositioned so as to be substantially even with the ablation catheter and this process continued until the blockage is traversed.

Some other methods of making a multi-layer catheter tube for a liquid core ablation catheter may use processes other than drip coating or dip coating for generating a low index of refraction film or layer on an inside surface of the catheter tube. For example, some embodiments of making a multi-layer catheter tube may include extruding a thin inner luminal layer of amorphous fluoropolymer onto a metal mandrel, etching an outer surface of the extruded inner luminal layer, applying a base layer tube configured as a water barrier over the etched outer surface of the inner luminal layer and applying a braided layer of thin metal filaments onto an outer surface of the base layer tube with the metal mandrel in place. Thereafter, an outer jacket layer may be applied over an outer surface and braided layer and an outer surface of the base layer tube and the metal mandrel removed from the inner luminal layer by stretching the metal mandrel to reduce an outer diameter thereof and withdrawing the metal mandrel from an inner lumen of the inner luminal layer.

Some embodiments of a method of making an inner luminal layer of a multi-layer catheter tube of a liquid core ablation catheter may include coating a metal mandrel with an over coat of an amorphous fluoropolymer solution and processing the coated mandrel at temperatures above a boiling point of a solvent of the amorphous fluoropolymer solution and above a glass transition temperature (Tg) of an amorphous fluoropolymer material of the amorphous fluoropolymer solution to drive off the solvent and anneal the amorphous fluoropolymer material and form an inner layer. Thereafter, the processed layer of amorphous fluoropolymer may be coated with one or more additional coats of amorphous fluoropolymer solution and the additional coat or coats processed at temperatures above the boiling point of the solvent of the fluoropolymer solution and above the glass transition temperature (Tg) of the fluoropolymer material of the fluoropolymer solution to drive off the solvent and anneal the fluoropolymer material to form a multi-layer inner luminal layer of sufficient thickness. An outer surface of the inner luminal layer may then be etched with an appropriate etching process to produce a bondable surface and a base layer tube configured as a water barrier applied over the etched outer surface of the inner luminal layer. A braided layer of thin metal filaments may also be applied onto the etched outer surface of the inner luminal layer with the metal mandrel in place and an outer jacket layer applied over the etched outer surface and braided layer. Once the outer jacket has been applied, the metal mandrel may be removed from the inner luminal layer by stretching the metal mandrel to reduce an outer diameter thereof and withdrawing the metal mandrel from an inner lumen of the inner luminal layer.

Some embodiments of a method of making a multi-layer catheter tube for a liquid core ablation catheter include applying a base layer tube configured as a water barrier onto a metal mandrel, applying a braided layer of thin metal filaments onto an outer surface of the baser layer tube with the metal mandrel in place and applying an outer jacket layer over an outer surface and braided layer and an outer surface of the base layer tube. The method may also include removing the metal mandrel from the inner luminal layer by stretching the metal mandrel to reduce an outer diameter thereof and withdrawing the metal mandrel from an inner lumen of the inner luminal layer. The method may also include drip coating a solution of amorphous fluoropolymer(s) onto an inside surface of the base layer and removing a solvent of the solution of amorphous fluoropolymer(s) to form an inner luminal layer of amorphous fluoropolymer(s).

Some embodiments of a laser catheter system to ablate blockages in body lumens using high energy and high power short duration laser pulses, include a high energy, high power short duration ultraviolet pulsed laser source and a low profile, kink resistant, torqueable liquid core ablation catheter operatively coupled to the laser source. The liquid core ablation catheter may include an elongate multi-layer catheter tube including a thin inner luminal layer of a low IR, U.V. transparent, amorphous fluoropolymer having an index of refraction of less than or equal to about 1.33 disposed on an inside surface of the base tubular layer. The ablation catheter may also include an ultraviolet grade output optical window or window assembly sealed to a distal end of the catheter tube and an ultraviolet grade input optical window sealed to a proximal end of the catheter tube to create a fluid tight core liquid volume. Further, a biocompatible U.V. transparent fluid may be disposed within and completely filling the core liquid volume formed between an inner surface of the thin inner luminal layer, the output optical window and the input optical window.

Some embodiments of a high energy laser coupler have a coupler body including a proximal section with a cylindrical outer surface, an inner bore disposed concentrically within the cylindrical outer surface and extending distally from a proximal end of the coupler body, a window connector bore disposed at a distal end of the inner bore, and a distal section extending distally from the window connector bore. Such laser coupler embodiments may also have a window connector body including a proximal section with a cylindrical outer surface configured to fit closely with an inside surface of the window connector bore of the coupler body, a flange portion disposed at a distal end of the proximal section, a stepped portion extending distally of the flange portion and an inner bore extending the length of the window connector body from a proximal end to a distal end thereof. An optical input window may be disposed within and secured to the inner bore of the window connector body such that a proximal end of the optical input window extends proximally from a proximal end of the proximal section of the window connector body. In addition, a flexible waveguide catheter tube including a proximal portion thereof may be disposed over the stepped portion of the window connector body and a cylindrical metal sleeve may be disposed over the proximal portion of the flexible waveguide catheter tube so at to secure the catheter tube to the stepped portion of the window connector body.

Some embodiments of a liquid core ablation catheter package assembly include a thin walled hermetically sealed enclosure having an interior volume and a material suitable for gamma sterilization. The package also includes a liquid core ablation catheter disposed within the interior volume of the hermetically sealed enclosure and a liquid disposed within the interior volume which is configured to maintain a vapor pressure within the interior volume sufficient to prevent loss of a liquid of a liquid core of the liquid core ablation catheter due to diffusion of the liquid core into the interior volume.

Some embodiments of an ablation catheter include an elongate catheter body, a transmissive core which is configured to transmit high energy laser light and which extends longitudinally from a proximal end to a distal end of the elongate catheter body, and an input surface in optical communication with the transmissive core at a proximal end of the elongate catheter body. The ablation catheter may also include an output surface in optical communication with the transmissive core at a distal end of the elongate catheter body. The ablation catheter may also have a tapered metal housing which includes a distal end having an inner bore that is disposed about the output surface, which includes a distal end that is longitudinally coextensive with a distal end of the output surface, which includes a tapered distal section that terminates distally with a thin wall that facilitates passage of a distal end of the ablation catheter through a lumen within a patient's body and which is configured to be sufficiently radiopaque in such as to be viewable by fluoroscopic imaging during a medical procedure.

Certain embodiments are described further in the following description, examples, claims and drawings. These features of embodiments will become more apparent from the following detailed description when taken in conjunction with the accompanying exemplary drawings.

BRIEF DESCRIPTION OF THE DRAWINGS

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

FIG. 22 is an elevation view of a distal portion of a support catheter embodiment having an angled distal section configured for nutation of an ablation catheter disposed therein.

FIG. 23 is an end view of the support catheter of FIG. 22.

FIG. 24 is a schematic representation of an annular area of ablation swept by the distal end of the liquid core ablation catheter while undergoing nutation due to rotation of the angled support catheter of FIG. 22.

FIG. 25 is a schematic representation of a circular area of ablation swept by the distal end of the liquid core ablation catheter while undergoing nutation due to rotation of the angled support catheter of FIG. 22.

FIG. 46 is an enlarged elevation view in partial section of a laser connector ferrule embodiment of FIG. 3 for use with a liquid core ablation catheter.

FIG. 47 is a transverse cross section view of the laser coupler of FIG. 46 taken along lines 47-47 of FIG. 46.

FIG. 48 is a transverse cross section view of the laser coupler of FIG. 46 taken along lines 48-48 of FIG. 46.

DETAILED DESCRIPTION

Figure 3:
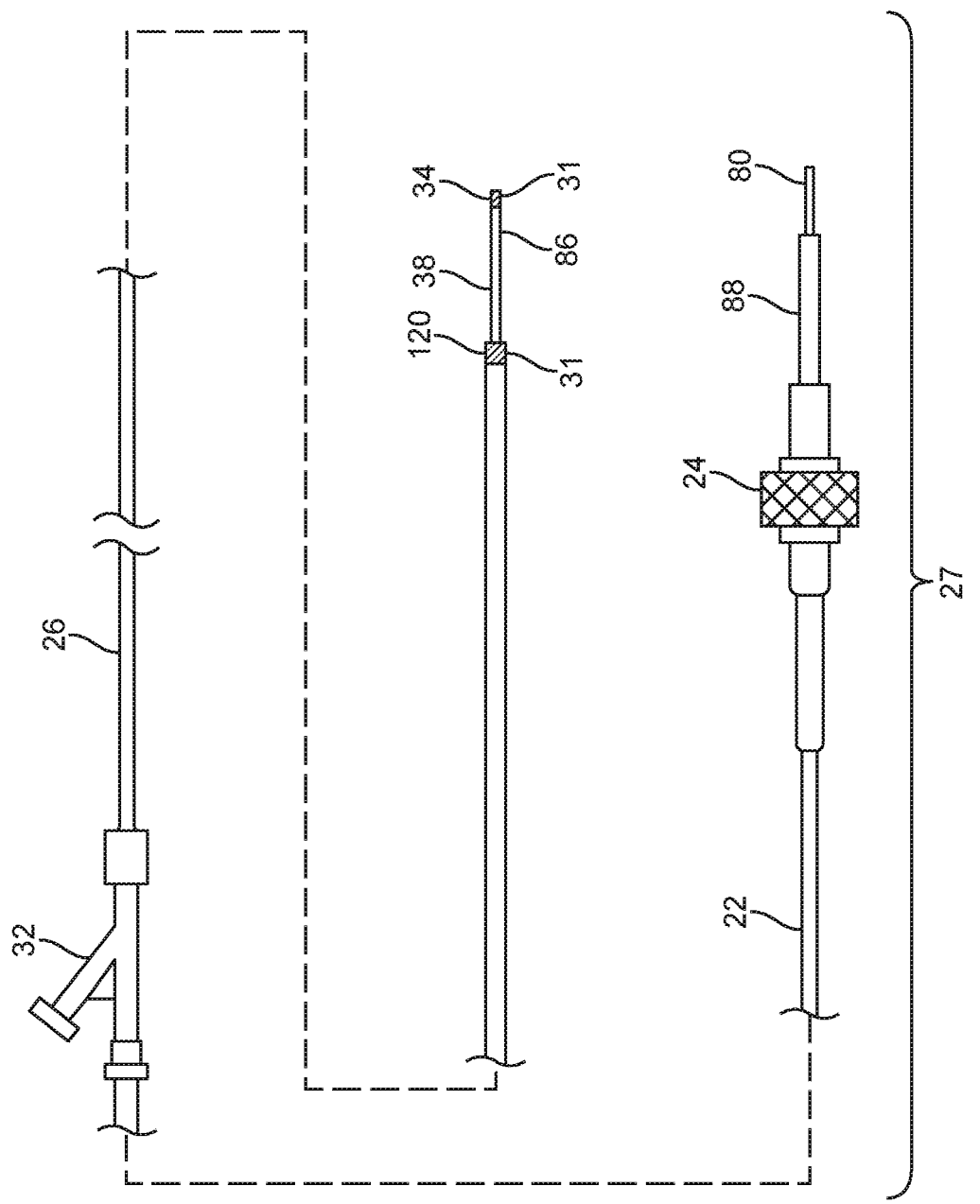
FIG. 3 is an elevation view of an embodiment of a laser catheter system including a liquid core ablation catheter disposed within a support catheter, the support catheter having a saline flush port.

As discussed above, laser catheters and laser delivery systems in general have wide range of applications in the medical field. Such systems may be used to deliver laser energy to desired sites of a patient's anatomy, and may be particularly suitable for delivering laser energy to locations within a patient's body that allow for minimally invasive treatment of a variety of indications using a variety of treatment modalities. Examples of some laser treatment modalities include heating tissue, stimulating tissue, drug activation within a patient's tissue and ablation of tissue. Some examples of clinical indications for laser treatment may include laser atherectomy. One drawback of some current laser systems is the cost of the systems and devices used to deliver the laser energy, particularly with regard to those components that are designated as single use products. Liquid core catheter embodiments 22, as shown in FIG. 3, may generally be considerably less expensive than a silica fiber optic based catheter and may also have less dead space in the cutting area at the distal end of the catheter. The reduced dead space (that distal surface area that is not emitting laser energy) may be an important feature for ablation of blockages in arteries and for the ability of the catheter to cross a lesion in a patient's vessel.

Figure 18:
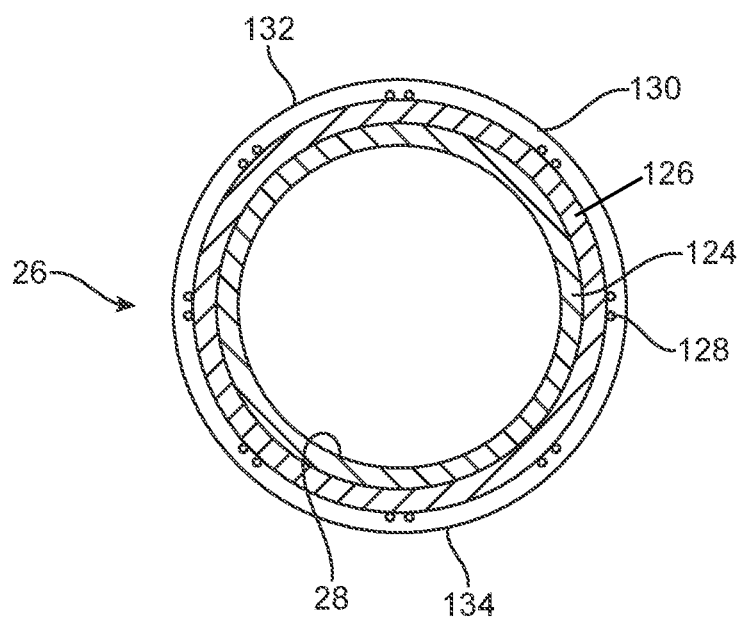
FIG. 18 is a transverse cross section view showing an embodiment of the support catheter of FIG. 4 and taken along lines 18-18 of FIG. 4.

FIGS. 1-27 show a laser ablation system embodiment 8 that includes a laser energy source 10 including a housing 12, a power cord 14, an activation footswitch 16, a control panel 18 and an output coupler 20. A liquid core ablation catheter 22 has a laser coupler 24 which is disposed at a proximal end 30 of the ablation catheter 22 and which is coupled to the output coupler 20 of the laser source 10. The ablation catheter 22 is disposed within an inner lumen 28 (as shown in FIG. 18) of a support catheter 26 which may be used to guide or support the ablation catheter 22 within a body lumen of a patient. The support catheter 26 includes a Y-adapter 32 coupled to a proximal end 30 thereof. The liquid core ablation catheter 22 is disposed within and passes through a central lumen (not shown) of the Y-adapter 32 as well. The support catheter 26 and ablation catheter 22 each may have a radiopaque marker 31 disposed at a respective distal end thereof. A working length of the liquid core ablation catheter 22 may include the length inside the patient's body between the access point and the target lesion site and the length outside the body necessary to couple or pass through the Y connector 32. An additional length may be needed to couple this working distance of about 90 cm to about 120 cm to the laser source 10 in some cases. If a laser source is large and located away from the patient, an additional length of waveguide may be necessary. Some laser catheter embodiments may be about 2 meters to about 3 meters long in some cases. In some cases, the laser source 10 of the laser system 8 may include a XeCl excimer laser which produces high energy pulses at a wavelength of about 308 nanometers, however, other high energy pulsed ultraviolet laser sources may be used. Some laser source embodiments 10 may have a pulse width of less than about 50 nanosec and a repetition rate of up to about 100 Hz. Some such laser source embodiments 10 may be capable of producing about 20 to about 100 mJ/pulse.

For some embodiments, the laser system 8 may also include an aiming diode (not shown) for applications where locating the distal tip 34 of liquid core ablation catheter 22 visually may be desirable. For some embodiments, a red color diode light source (not shown) may be used. This red diode wavelength may have a wavelength that is configured to penetrate some tissue types and may provide visibility of the distal tip 34 of the liquid core ablation catheter 22 and its position in the leg anatomy. The red diode light source may be located in the laser coupler 20 of the laser source 10 and coupled to the liquid core ablation catheter 22 by turning mirror or beam splitter (not shown) in some cases.

Figure 2:
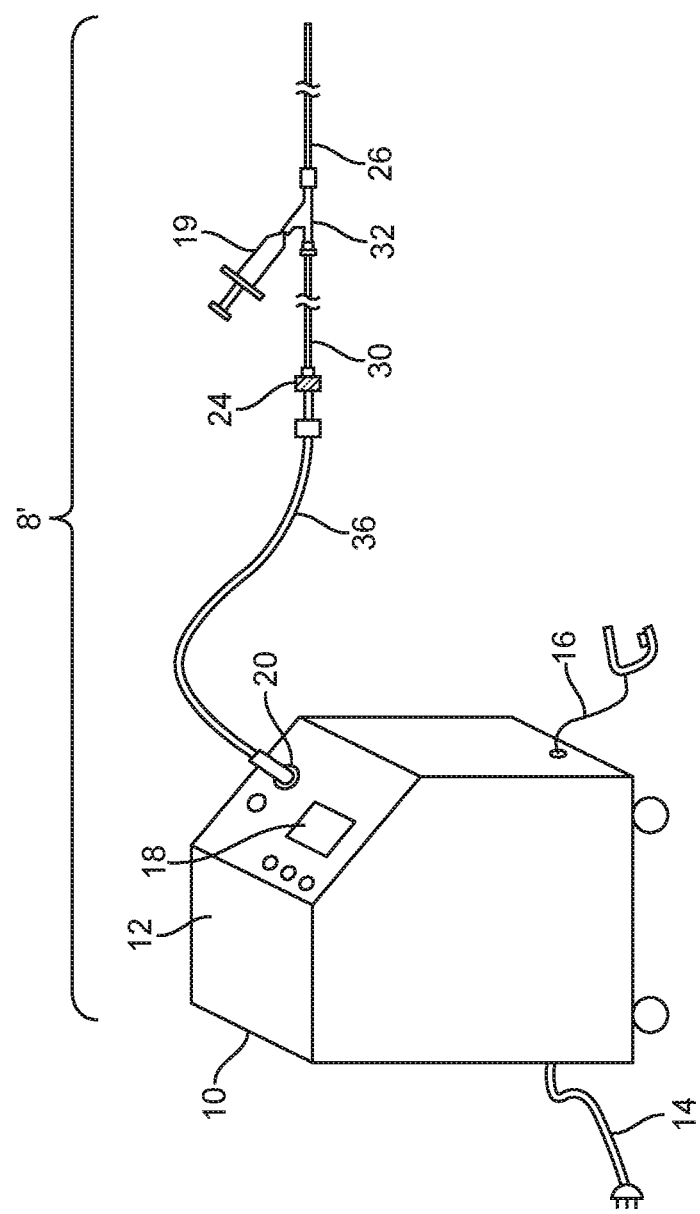
FIG. 2 is a perspective view of a laser system embodiment including a reusable extension waveguide connected between a laser and a disposable liquid core ablation catheter.

Since some ablation catheters 22 are generally disposable or single use only, the long 2-3 meter working length may be costly. For embodiments discussed herein, a robust liquid filled extension waveguide 36 for coupling from the laser source 10 to the single use disposable liquid core ablation catheter 22 may be used outside a patient's body and be designed to last for multiple uses. Such an optional extension waveguide 36, as shown in FIG. 2, may be used to connect the laser source 10 of the laser system 8' to a single-use liquid core ablation catheter 22 and have a length suitable to reach from the laser source 10 to the patient table (not shown). In some cases, the extension waveguide 36 may have a length of about 75 cm to about 300 cm, more specifically, about 75 cm to about 150 cm. The extension waveguide 36 may also be configured to contain a higher IR liquid core fluid than disposable liquid core ablation catheter embodiments 22 because it is generally disposed and used outside the patient's body and is not subject to some of the same design constraints as discussed above. As such, core liquids that have a higher IR may be used that may not be biocompatible in some cases.

Figure 1:
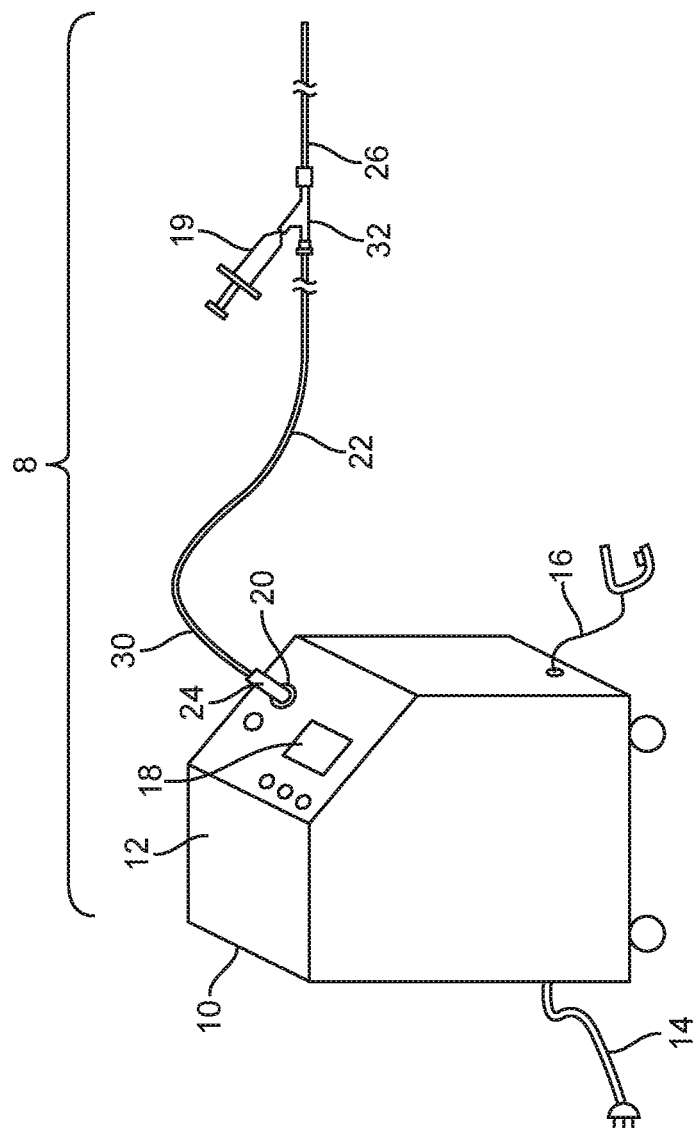
FIG. 1 is a perspective view of a laser system embodiment including a laser and a disposable liquid core ablation catheter coupled to the laser.
Figure 13:
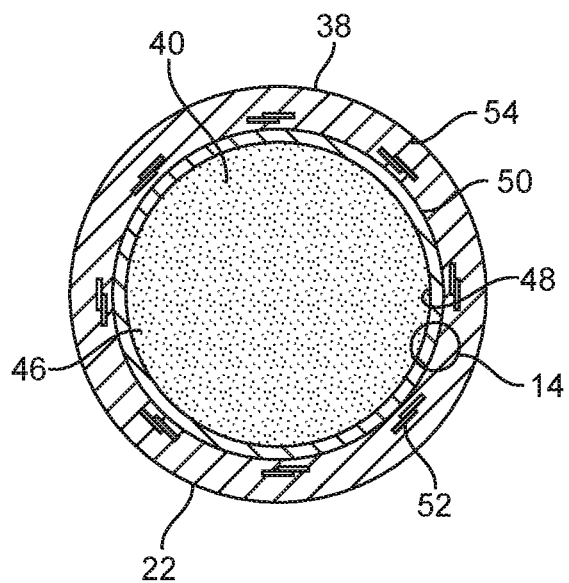
FIG. 13 is a transverse cross section of the liquid core ablation catheter embodiment of FIG. 5 taken along lines 13-13 of FIG. 5.

With regard to laser system embodiments 8 such as those shown generally in FIGS. 1 and 2, there are some features of the ablation catheter system 27, which includes the liquid core ablation catheter 22 and support catheter 26, shown in more detail in FIG. 3, that may be desirable or even necessary in some cases to function as desired. The liquid core ablation catheter 22, as shown in more detail in FIGS. 3, 5, 6, 8 and 10, includes a multi-layer catheter tube 38 having a low profile to fit inside particular blood vessels, which may have inner luminal diameters or inner transverse dimensions that vary in size from about 2 mm to about 6 mm. The wall thickness of the multi-layer catheter tube 38 of the liquid core ablation catheter 22 may be thin relative to a transverse dimension of the liquid core 40, as shown in FIG. 13, to insure flexibility and to minimize the "dead space" between an outer distal surface 42 of the output window 82 (shown in FIG. 8) which emits tissue ablating energy and an outer dimension of the multi-layer catheter tube 38 which does not emit tissue ablating energy. The non-emitting wall of the catheter tube 38 forms the "dead space" that does not contribute to tissue cutting or ablation. As such, the ablation catheter 22 has a large fraction of cutting area relative to the overall area of the distal tip or surface of the ablation catheter. This may be achieved by having a multi-layer catheter tube 38 with a thin wall thickness as shown in FIG. 13.

For some embodiments, the multi-layer catheter tube 38 of the ablation catheter 22 is flexible enough to maneuver around bends in a patient's artery without kinking yet be stiff enough to be able to push the ablation catheter 22 through the vessel while ablating blockages. In some cases, the catheter tube 38 is able to be torqued and rotated at the distal end of the catheter tube 38 from a proximal portion 39 of the catheter tube 38 that extends outside the patient's body.

In some cases, the core fluid 40 used in the ablation catheter 22 is transparent in the ultraviolet laser energy wavelengths and may be a biocompatible fluid in case of accidental leakage from the catheter 22. In addition, the configuration of fluid core ablation catheter 22 may be capable of transmitting high power pulses above a tissue ablation threshold in the ultraviolet wavelength range preferably with pulse widths shorter than 50 nsec and at repetitions rates of up to 100 Hz in order to achieve the desired results in some cases. For some indications, the liquid core ablation catheter 22 may be designed for single use only but may also have a long shelf life after sterilization of typically one year or more for use in a clinical setting. Therefore, the core liquid 40 disposed in the inner lumen 46 of the ablation catheter 22 should not diffuse out of the thin wall multi-layer catheter tube 38 of the catheter system 27, as shown in FIG. 3, over this type of time period for some embodiments. Also, for some embodiments, the materials of the multi-layer catheter tube 38 may be sterilizable without significant degradation or degradation that would render the ablation catheter 22 unusable. Gamma or X-ray sterilization may be ideal in some situations and may be useful in order to ensure that any fluid, such as liquid water used for a transmissive core, inside the ablation catheter is sterilized.

Figure 14:
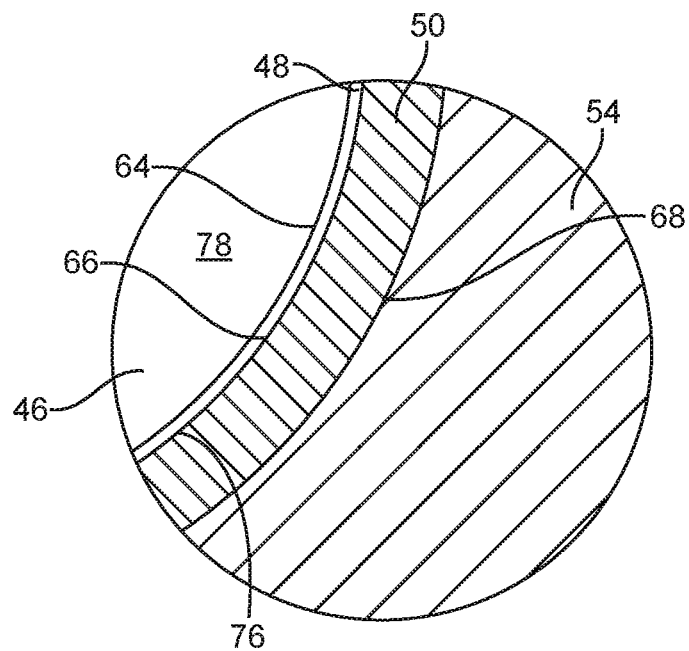
FIG. 14 is an enlarged view in section of the wall of the liquid core ablation catheter of FIG. 13 indicated by the encircled portion 14 in FIG. 13.

For some embodiments, the transmission of laser energy through the liquid core ablation catheter 22 is high enough to enable a relatively small laser source to be used for the laser system 8 in order to save cost. For some indications, the ablation catheter 22 allows sufficient transmission to achieve a minimum output energy per pulse to ablate differing arterial plaque types. In some cases, such a minimum output energy may range from about 4 milli-Joules/mm$^2$ (mJ/mm$^2$) to about 14 mJ/mm$^2$ for a XeCl laser at a wavelength of about 308 nanometers (nm) and an approximate pulse width of about 10 nanoseconds (nsec) in some cases. Longer 308 nm laser pulses of about 100 nsec may have slightly higher ablation thresholds for the same tissue types. As such, a fluid for the core of the liquid filled waveguide may transmit high power and high pulse energy ultraviolet excimer laser pulses in some cases and may be biocompatible for insertion into human arteries. Pure water and normal saline (0.9% NaCl aqueous solution) are highly transparent and are biocompatible but they both have very low indices of refraction (IR) compared to the IR of most polymer tubing materials used in liquid waveguide catheters. For example, at a temperature of about 20 degrees C., water has an IR of about 1.333 in the visible wavelength region and normal saline has an IR of about 1.335. Teflon® fluorinated ethylene propylene (FEP) tubing may have an IR in the visible range of light of about 1.338 which may be too high to produce an effective waveguide using water or saline for some ablation catheter embodiments 22. This is because the IR of the inner luminal layer 48 of the catheter tube 38 as shown in FIG. 14, must be less than the IR of the fluid core 40 to achieve total internal refraction of laser energy being guided by the liquid core ablation catheter.

Embodiments of the catheter system 27 may be used for navigation within the tortuous anatomy of a patient's vasculature may include a multilayer design or designs. In some cases, a central catheter tubing core 50 may be braided with a metal wire or ribbon 52 and this portion may have an over jacket 54 as shown in FIG. 13. This type of design may be used for applications that require high torque, burst pressure resistance, pushability, steerability and kink resistance. The physical characteristics of such a braided catheter embodiment 27, as shown in FIG. 3, may be varied by using different durometer values for the plastic tubing of the catheter body and by varying the pitch and thickness for the metal braid. This basic design concept may be applied to the unique characteristics of liquid core ablation catheter embodiments 22.

Figure 15:
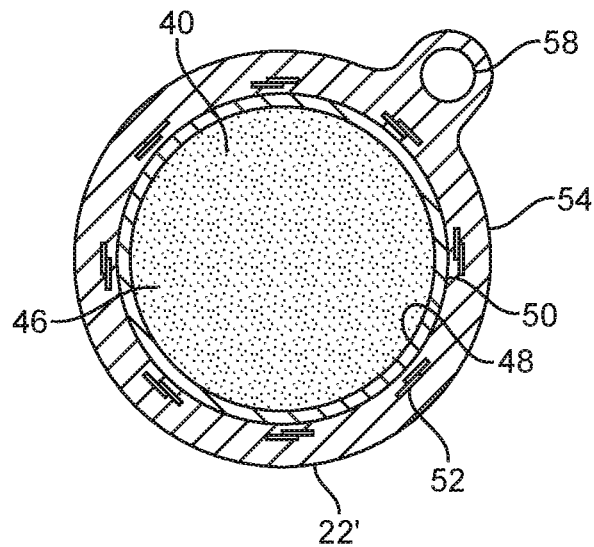
FIG. 15 is a transverse cross section view of an embodiment of a liquid core ablation catheter with an eccentric guidewire lumen.
Figure 16:
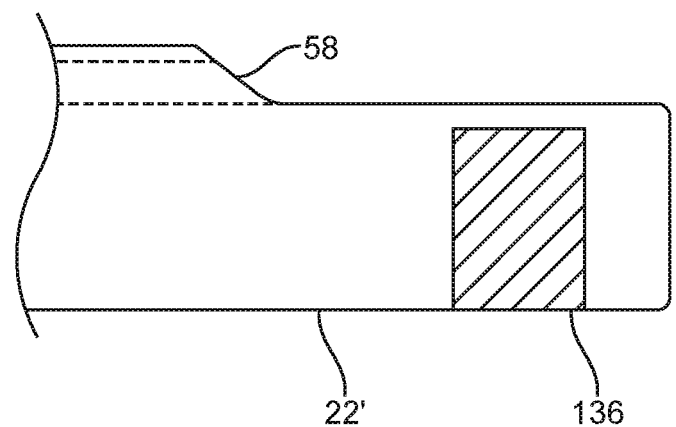
FIG. 16 is an elevation view of a distal portion of the liquid core ablation catheter embodiment of FIG. 15.
Figure 17:
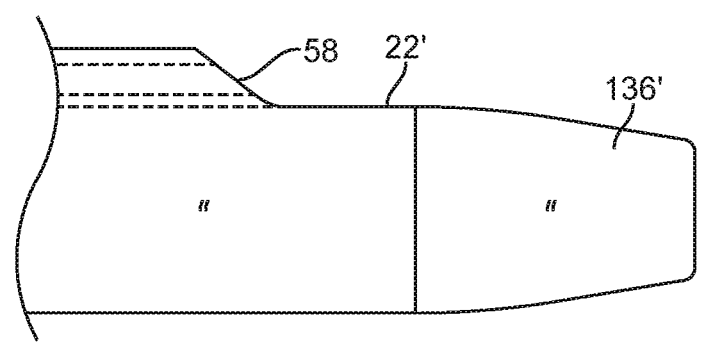
FIG. 17 is an elevation view of a distal portion of an embodiment of the liquid core ablation catheter embodiment of FIG. 15 having a tapered metal housing disposed at a distal end thereof.
Figure 26:
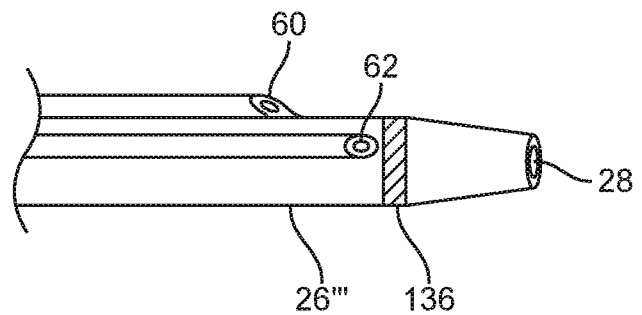
FIG. 26 is a perspective view of a distal portion of an embodiment of a multi-lumen support catheter having two eccentric guidewire lumens.
Figure 27:
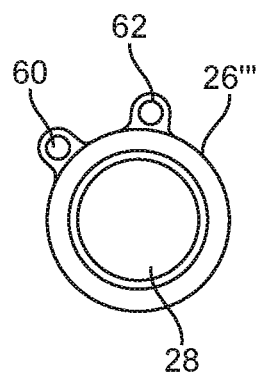
FIG. 27 is an end view of the support catheter embodiment of FIG. 8A.
Figure 31:
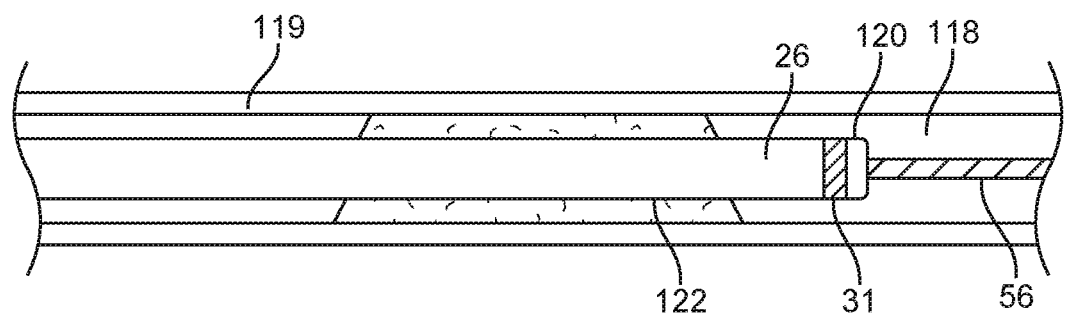

In some cases, the laser ablation catheter system 27 includes means of guidance of the ablation catheter through a vessel lumen or blockage thereof, such as an arterial blockage. Guidewire 56, as shown in FIG. 31, which is disposed in a concentric or eccentric position within a vessel 119 may be used in some cases and may pass through one or more guidewire lumens, such as guidewire lumen 58 of the liquid core ablation catheter embodiment 22' as shown in the embodiments of FIGS. 15 and 16. The ablation catheter 22' includes an eccentric guidewire lumen 58 disposed along an outer surface of the ablation catheter 22. The guidewire lumen may have a distal port disposed proximally from a distal end of the ablation catheter 22' by at least about 5 mm. The guidewire lumen 58 may have a longitudinal length of at least about 10 cm. Support catheter embodiments 26''' including one or more guidewire lumens such as the two guidewire lumens 60 and 62, as shown in the embodiments of FIGS. 26 and 27, may also be used to guide and support the ablation catheter.

Figure 19:
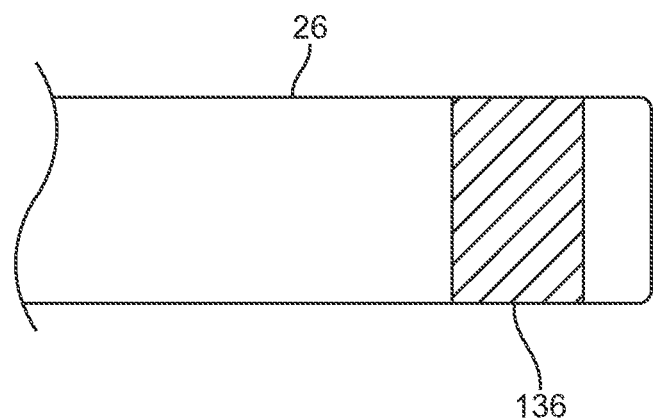
FIG. 19 is an elevation view of a distal portion of the support catheter embodiment of FIG. 18.
Figure 20:
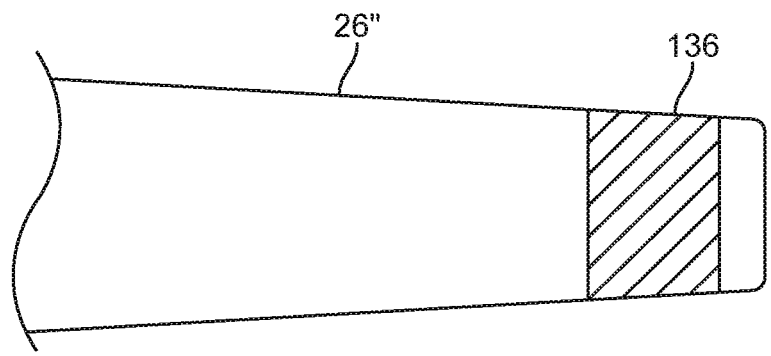
FIG. 20 is an elevation view of a distal portion of a support catheter embodiment that includes a tapered distal portion.
Figure 21:
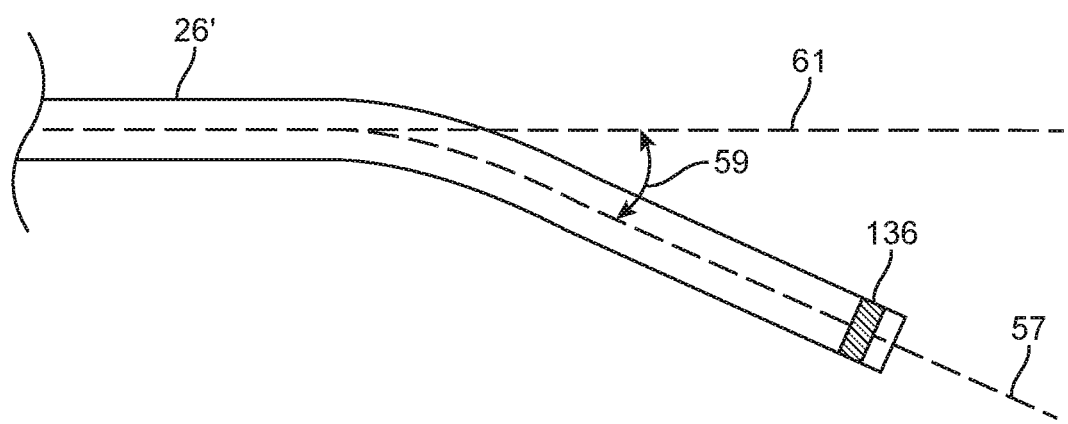
FIG. 21 is an elevation view of a distal portion of a support catheter embodiment that includes an angled distal end.

In addition, straight support catheters 26 as shown in FIG. 19 or angled support catheters 26' as shown in FIG. 21, may be used for guiding a liquid core ablation catheter 22 through restenosed stents in that the stent itself may serve as a guide to prevent the ablation catheter 22 from causing an arterial wall perforation. Some support catheter embodiments may include a tapered support catheter embodiment 26", angled support catheter embodiment 26' or profiled support catheter embodiment as shown in FIGS. 20 and 21 to help center the liquid waveguide ablation catheter 22 remain in the vessel lumen 118 during use as shown for example in FIGS. 28-32. The angled support catheter embodiment 26' as shown in FIG. 21, may have an angled distal tip with a discharge axis 57 disposed at an angle, indicated by arrow 59, with respect to a nominal longitudinal axis 61 of the support catheter 26'. For some embodiments, the angle 59 of the discharge axis of the support catheter 26' may be about 5 degrees to about 45 degrees, more specifically, about 10 degrees to about 30 degrees.

Figure 36:
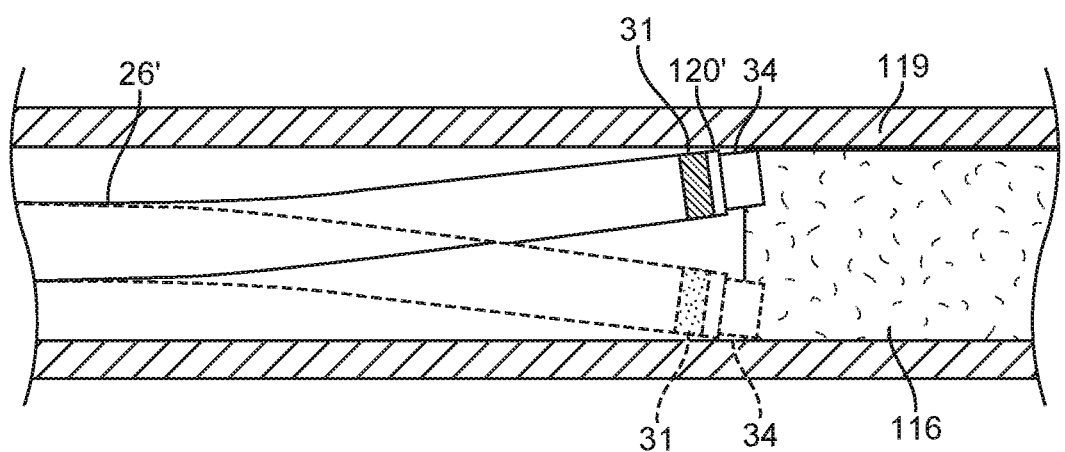
FIG. 36 is an elevation view in partial section illustrating creation of an annular area of ablation of a vessel blockage by nutation of an ablation catheter as shown in FIGS. 22-24.

In addition, an angled support catheter embodiment 26', as shown in FIGS. 22-25, may be rotated about its longitudinal axis, as shown by arrow 65 in FIG. 22, over an ablation catheter, such as liquid core ablation catheter 22, which extends distally therefrom. Such rotation of an angled support catheter 26' with a deflected distal section may result in orbiting or nutation of the distal tip of ablation catheter 22 during the ablation process, i.e. during emission of ablation energy suitable for tissue ablation from the distal end of the liquid core ablation catheter 22. This nutation of the ablation energy emitting surface of the liquid core ablation catheter 22 may produce a band or annulus of ablation or tissue removal as shown in FIG. 24. Such a process is also illustrated in the elevation view of a tissue ablation process shown in FIG. 36. The band or annulus of ablation produced by such and configuration and method may be suitable to create a larger neo-lumen or passage through a lumenal obstruction or constriction than would be possible by pushing the same liquid core ablation catheter 22 directly through the obstruction or constriction in a straight line. Although FIGS. 24 and 36 illustrate a band or annulus of ablation carried out by nutation of the support catheter 26' about the liquid core ablation catheter 22, a circular area of ablation may also be generated for rotations with lesser nutation magnitudes as shown in FIG. 25. In such cases, some portion or portions of the emitting surface of the distal end of the liquid core ablation catheter 22 would be disposed over a center of the neo-lumen being ablated into the obstructive tissue. In such cases, the neo-lumen may still be substantially larger than an outer surface of the emitting surface or outer transverse dimension of the liquid core ablation catheter 22. In some instances, the angled distal section of the angled support catheter 26' may have a length, as shown by arrow 63 in FIG. 22, of about 5 mm to about 50 mm, more specifically, about 5 mm to about 15 mm. In some cases, a discharge angle as indicated by arrow 59' in FIG. 22 may be about 3 degrees to about 10 degrees.

In some cases, the numerical aperture of a liquid core ablation catheter 22 may be above a certain minimum value in order to prevent losses in the catheter, particularly due to bending of the catheter. The numerical aperture of the liquid core ablation catheter 22 depends to a large extent on the difference between the IR of the core liquid 40 and the IR of an inner luminal layer 48 of the multi-layer catheter tube 38.

The inner luminal layer 48 is a tubular layer of material or materials of the catheter tube 38 which surrounds the core liquid 40 within the liquid core ablation catheter 22. The inner luminal surface 64 (shown in FIG. 14) of the inner luminal layer 48 is the surface that contacts the core liquid 40. It is the interface between the core liquid 40 and the inner luminal layer 48 that may be configured to generate total internal refraction of laser light disposed and propagating within the core liquid 40. As such, in some cases, the IR of the core liquid 40 should be greater than an IR of the inner luminal layer 48 of the catheter tube 38 by at least about 0.02.

The inner luminal layer 48 of the catheter tube 38 may also be transparent or substantially transparent to the wavelength of laser energy being transmitted through the core liquid 40. This may be particularly desirable because the U.V. radiation refracting at the core liquid 40 inner luminal layer 48 interface may extend into the inner luminal layer 48 (and possibly beyond the inner luminal layer 48 of the multi-layer catheter tube 38) by a distance of about several wavelengths during the refraction process. When the refracted light extends into the inner luminal layer 48 (or any other subsequent layers of the multi-layer catheter tube 38 such as the base layer tube 50 as shown in FIG. 14) during the refraction process it may be strongly absorbed if the material of the inner luminal layer 48 is not transparent or substantially transparent to the wavelength and energy density of the refracted light. This means that many materials may be incompatible for use as an inner luminal layer 48 of the multi-layer catheter tube 38 of the liquid core ablation catheter 22, particularly for embodiments using a core liquid 40 of water or normal saline.

In view of the foregoing, inner luminal layer embodiments 48 may be generated by coating an internal surface 66 of the base layer 50, as shown in FIG. 14, of a multi-layer catheter tube 38 made from common catheter materials with a film of material having an IR of less than about 1.33. As discussed above, it may be important for such a coating material to be transparent or substantially transparent to the ultraviolet wavelength used in the corresponding catheter. In addition, the inner luminal layer 48 may also have a sufficient wall thickness to retain the high power U.V. laser energy and prevent substantial losses through the inner luminal layer 48 to those layers of the catheter tube 38 surrounding the inner luminal layer 48 as for some embodiments, the surrounding tubular layers may include materials which absorb the U.V. laser energy and may be damaged or destroyed by it.

Certain amorphous fluoropolymers may be used as coatings having a low IR relative to some core liquids 40 and thus may be used for the generation of an inner luminal layer 48 of catheter tubes 38. DuPont® Corporation located in Wilmington Del. has developed certain coatings including, in particular, fluorinated (ethylenic-cyclo oxyaliphatic substituted ethylenic) copolymer (Teflon AF®) which is a family of amorphous fluoropolymers based on copolymers of 2,2-bistrifluoromethyl-4,5-difluoro-1,3-dioxole (PDD) and tetrafluoroethylene (TFE). According to DuPont, the principle differences between the various grades of Teflon AF® are based solely on the relative amounts of TFE to PDD in the polymer chain. Teflon AF® polymers have the lowest index of refraction of any known polymer and are substantially transparent to light, even at U.V. wavelengths making these materials suitable as low index coatings for waveguide applications. In some cases, these amorphous fluoropolymers may be formulated with different IRs. Teflon AF 2400® has a TFE to PDD ratio of about 11:89 and a particularly low IR of about 1.29 in the visible light wavelength range. Teflon AF 1601® has a TFE to PDD ratio of about 36:65 and an IR of about 1.31 at the visible light wavelength range. Either of these formulations may be used to form an inner luminal layer 48 of the multi-layer catheter tube 38 of the ablation catheter 22. It should be noted that the IR of these fluorinated polymers as well as the IR of water and normal saline, increase in value for UV wavelengths relative to values for light in the visible wavelength range.

We have measured the transmission of 308 nm laser pulses through both water and saline filled tubes of uncoated Teflon® FEP and observed that the light was lost in the first foot of the tube. Pulses having a wavelength of about 308 nm may be readily transmitted through a meter long FEP tube filled with the same fluids when the tube was lined with Teflon AF 1601®. Therefore, in the UV the IR difference between water or saline and the Teflon AF 1601® or Teflon AF 2400® appears to be sufficient for total internal refraction and high transmission of short pulse laser energy having a pulse width of less than about 50 nsec and a wavelength of about 308 nm.

These amorphous fluoropolymers discussed above may be soluble in selected solvents to facilitate coating processes. In some cases, these amorphous fluoropolymer coatings adhere best to fluorocarbon polymers but not very well to other plastic types. As such, when using an amorphous fluorinated polymer material for an inner luminal layer 48 of the embodiments herein, the choice of suitable materials for the remaining layers of the catheter tube 38 may be limited. These and other properties of the amorphous fluorinated polymer materials may also create difficulties for construction of suitable catheter tubes 38 utilizing amorphous fluorinated polymer materials for the inner luminal layer. For example, Teflon AF 2400® which has an IR of about 1.29 is generally produced in a 1% solution which may be too dilute to achieve a sufficient coating thickness to confine U.V. laser energy to the core liquid 40 and inner luminal layer 48. Teflon AF 1601® with concentrations up to about 18% may be used to produce a coating for an inner luminal layer 48 with sufficient thickness to confine U.V. laser energy at 308 nm wavelength and with an IR of about 1.31.

Teflon® FEP tubes may not be as suited for use with liquid filled laser waveguides 22 because water and aqueous solutions of saline over time will diffuse out of the FEP tube in low humidity environments. As an example, we filled a thick wall tube of Teflon® FEP with water, sealed the ends and placed it in an oven at 50 degrees C. and saw bubble formation within 10 days. In some cases, we might prevent this diffusion of water by placing the FEP water filled tube in a plastic enclosure which contains water. In some cases, catheters 22 may be placed in an oven at about 50 degrees C. to about 60 degrees C. for several months to perform accelerated lifetime testing to simulate a one year shelf life. Therefore, the multi-layer catheter tube 38 of the ablation catheter 22 must not have a high permeability for water transfer at oven temperatures of about 50 degrees C. to about 60 degrees C. to qualify as a medical catheter for long shelf life in some cases. In addition, for some applications, the tubing material or materials of the multi-layer catheter tube 38 and/or support catheter 26 should be able to be sterilized with gamma radiation or x-rays. Teflon® FEP is generally not as suitable for radiation sterilization.

Another disadvantage with using an FEP tube liner may be that the hardness shore durometer of about 55D is about half that of PCTFE which may have a shore hardness of about 85D to about 95D. When the FEP liner is thin and has a low durometer then there may be an impression of thin elements of a braid material 52 used on an outside surface 68 (shown in FIG. 14) of a base tube 50 of the multi-layer catheter tube 38 to transfer into the inner luminal surface 64 of the inner luminal layer 48 which may cause the light to be scattered out of the tube. Also, when an ablation catheter 22 is placed in the Y adapter 32 and a corresponding hemostatic valve thereof, the valve may compresses a low durometer ablation catheter embodiment 22, distort the wall structure of the ablation catheter and hinder transmission of light therethrough.

We have found that polychlorotrifluoroethylene, PCTFE, has one of the lowest diffusion rates for water compared to other polymer plastics, and can be coated with Teflon AF® solutions and can also be sterilized using radiation. We filled a thin wall PCTFE tube with water and sealed the ends of the tube and placed the sealed assembly in an oven at 60 degrees C. for one month. No diffusion of the water in the PCTFE tube was apparent even after the one month dwell time in the oven. As such, PCTFE may be used in some cases for certain layers of the multi-layer catheter tube 38.

The higher durometer for PCTFE of about 90 D even with thin walls of about 0.002" may provides extra stiffness that resists penetration or transfer of a braid pattern onto an inner luminal surface 64 of the inner luminal layer 48 a liquid core ablation catheter 22. This higher durometer may also add stiffness and pushability to the multi-layer catheter tube 38, but might kink easily in some cases without the metal braid 52. PCTFE tubing does have a draw back in that the maximum working temperature of the material may be about 125 degrees C. in some cases. For some embodiments, the ablation catheter 22 may include a multi-layer catheter tube 38 an outer layer or over-jacket 54, as shown in FIGS. 13 and 15, having a lower hardness durometer of about 65D to about 75D, more specifically, about 70D. In some cases, the outer layer or over-jacket layer 54, as shown in FIG. 13, may have to be processed at a temperature level where the PCTFE wall of the base tube is not compromised. This may have the effect of substantially limiting the choice of materials and processing methods for the over-jacket 54 for the multi-layer catheter tube 38 of the liquid core ablation catheter 22.

There are several options for forming the inner luminal layer 48 of the multi-layer catheter tube 38 from an amorphous Teflon AF® or other suitable amorphous fluoropolymer on the inside of a base tube 50, such as a PCTFE or FEP base tube 50. One method of creating such an inner luminal layer 48 includes using a solution of Teflon AF® dissolved at percentages of about 1% to about 18% Teflon AF® solids in a suitable solvent such as Fluorinert solvent. One type of Fluorinert is a perfluorcarbon made by 3M Company under the description FC-40. The Fluorinert solvent may be offered in various formulations that have differing boiling points. In some cases, a Fluorinert solvent having a boiling point of about 155 degrees C. may be used for the processes discussed herein.

One or more coatings may be applied to the inside of the PCTFE tube and the solvent may then be evaporated off to leave a thin layer solid film of low IR of Teflon AF® of about 5 microns to about 50 microns thick, more specifically, about 5 microns to about 20 microns thick. Various Teflon AF® layers with differing IRs and concentrations may be applied or mixtures of differing solutions may be applied in a single mixed layer. Examples of amorphous coatings with low indices of refraction may include Teflon AF 1601®, Teflon AF 2400®, Cytop® manufactured by Asahi Glass Company located in Japan, and Hyflon AD 40® or Hyflon AD 60® made by Solvay Solexis Company located in Italy. Any of these amorphous fluoropolymers may be mixed with a high boiling point perfluoropolyether (PFPE) oil to provide thicker layers at lower cost. In some cases, a PFPE oil such as Fomblin YR 1800® sold by the Solvay Solexis Company may be used. The boiling point of such a PFPE oil may be about 220 degrees C. to about 275 degrees C. for some embodiments.

Regarding the processing of some inner luminal layer embodiments 48, the manufacturer recommends in some cases that these amorphous fluoropolymer coatings be annealed above the boiling point of the solvent used and then tempered for several minutes above the glass transition temperature, Tg, of the solid amorphous fluoropolymer film which may be about 160 degrees C. for Teflon AF 1601® and about 240 degrees C. for Teflon AF 2400®. Exposure to these temperatures might be detrimental for the PCTFE tube and other low melt plastics such as Pebax® used for the over-jacket 54 on the metal braid 52 of the multi-layer catheter tube 38 of the liquid core ablation catheter 22. In some embodiments, Pebax® materials may have a melting temperature of about 135 degrees C., which is well below the recommended processing temperatures to both remove the solvents and get the materials above the Tg of the amorphous fluoropolymer. Method embodiments discussed herein were specifically developed to enable the application of these films onto an inner luminal surface of a PCTFE tube (or the like) to create the inner luminal layer 48 of the ablation catheter 22. In some cases, these techniques use relatively lower process temperatures for longer time durations to achieve workable amorphous fluoropolymer inner luminal layers 48, as shown in FIG. 14, for multi-layer catheter tubes 22 which may then be filled with a liquid core 40 such as water or saline.

For some embodiments, a method of generating a multi-layer catheter tube 38 may include a drip coating method whereby a solution of amorphous fluoropolymer or mixtures thereof are dissolved in solution such as Fluorinert FC-40® from 3M at concentrations high enough to provide at least a 5 micron or more layer thickness per coat. One or more multi-layer catheter tubes 38 may be mounted vertically and cleaned on the inside luminal surface with isopropyl alcohol or the like. The inner luminal surface of the catheter tube 38 may then be coated with the solution of amorphous fluoropolymer for a given dwell time and annealed at temperatures less than about 100° C. or the melting point of the multilayer catheter material for times sufficient to remove all the solvent. In some cases, dwell time at temperatures of less than about 100° C. may be up to about 4 hours. The lower temperatures for annealing may be configured or otherwise selected in order to prevent thermal damage to the polymer materials of the multi-layer catheter tube 38 to which the coating is being applied. This drip coating process may be repeated multiple times to produce an inner luminal layer 48 thickness and uniformity that encapsulates or otherwise contains high power laser energy at a wavelength of about 308 nm in the resulting waveguide core of an ablation catheter 22 constructed from such a multi-layer catheter tube 38 and core-inner luminal layer junction therein. After processing, the multi-layer catheter tube 38 may be filled with an appropriate core liquid 40 and sealed with suitable windows at both proximal and distal ends thereof.

For some embodiments, the inner luminal layer 48 should also be thick enough to smooth out any surface irregularities on the inner surface of a drip coated tube, such as a base layer tube 50 made from PCTFE, FEP or the like. For some embodiments, a thickness of about 5 microns to about 15 microns for the low IR internal material of the inner luminal layer 48 might provide for an efficient coating. In some cases, Teflon® FEP or other fluoropolymer based materials may be used as an alternative to PTCFE for making base layer tubes 50 (see FIG. 14), however, there may be issues with regard to keeping core fluids 40, such as water core fluids, from diffusing out of the liquid core ablation catheter 22 during shelf life storage. Packaging the finished and sterilized liquid core ablation catheter 22 in a high humidity package may mitigate this problem in some cases, particularly in instances where FEP is used. Suitable materials for such a package may include an openable enclosure made from metal coated plastic, PCTFE or any other suitable material capable of producing a hermetic or hermetic type seal that is sealable about a finished ablation catheter or catheter system and is suitable for a desired type of sterilization such as gamma e-beam or the like.

Figure 8:
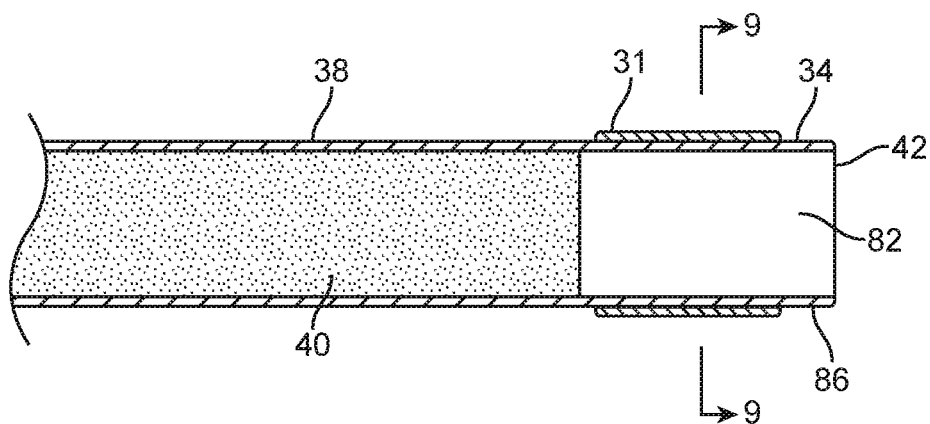
FIG. 8 is an elevation view in partial section of a distal portion of the liquid core ablation catheter embodiment of FIG. 3.
Figure 9:
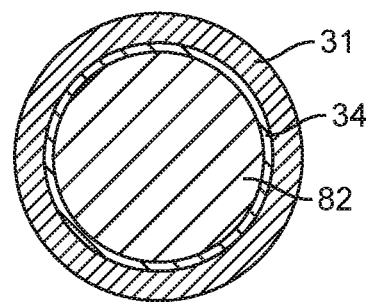
FIG. 9 is a transverse cross sectional view of the liquid core ablation catheter of FIG. 8 taken along lines 9-9 of FIG. 8.

Other methods for forming such a low index layer from these materials may include extruding a thin layer, for example, of solid Teflon AF 2400® or Teflon AF 1601®, over a smooth polished metal mandrel to form the inner luminal layer 48 of the multi-layer catheter tube 38 of the liquid core ablation catheter 22. In some cases, such an extruded thin layer of low index material may have a thickness of about 5 microns to about 50 microns. Once the amorphous fluoropolymer inner luminal layer 48 is extruded over the mandrel, the outer surface 76 (shown in FIG. 14) of the inner luminal layer 48 may then be etched to promote surface adhesion thereto. A thicker wall PCTFE base layer tube 50, or base layer tube 50 made from another suitable material, such as FEP, may then be over extruded onto the etched outer surface 76 of the inner luminal layer 48, followed by braiding of a multi-filament braid 52 over the outer surface of the PCTFE tube 50. Then an over-jacket 54 may be extruded over an outer surface of the braided layer 52 and PCTFE base tube 50. For some embodiments, the mandrel may then be removed from the multi-layer catheter tube embodiment 38. The tubular inner lumen 78 that remains once the mandrel has been removed may then be filled with transmissive liquid 40 and sealed with optical windows at each end, specifically an input optical window 80 at the proximal end 84 (shown in FIGS. 3 and 6) of the multi-layer catheter tube 38 and an output optical window 82, as shown in FIG. 8, at the distal end 86 (shown in FIG. 3) of the multi-layer catheter tube 38. The optical windows 80 and 82 may also be transparent to the wavelength of laser energy to be guided therein.

Some methods may include placing multiple coating layers of an amorphous fluorocarbon material dissolved in a solvent over a mandrel wire with heat annealing between layers to above the Tg of the polymer to form the inner luminal layer 48. The outer surface 76 of the inner luminal layer 48 may then be etched in order to facilitate adhesion thereto. A PCTFE base layer tube 50, or base layer tube 50 made from another suitable material, may then be over-extruded or otherwise applied over the outer surface 76 of the inner luminal layer 48 with a subsequent braid 52 applied to an outer surface of the base layer tube 68 and over jacket 54 added to an outer layer of the braid 52 and base layer tube 50 to complete the multi-layer catheter tube 38. In this example, all the high temperature annealing is done with a high temperature mandrel wire before the plastics are overlaid. No matter which method is used, the PCTFE base tube 68 is independent of the inner luminal layer 48 which may be a thin low IR coating where all the refraction of the guided laser energy takes place. In some cases, the thickness of this thin inner luminal layer 48 must be at least several wavelengths thick for refraction as discussed above.

This method may also include coating a mandrel wire with a concentrated solution of an amorphous fluoropolymer dissolved in a solvent. The percentage of solids may be greater than 10% for maximizing wall thickness per coating layer. The coated mandrel wire may then be annealed above the boiling point of the solvent, which may be FC-40 whose bp is 155° C. and then annealed up to 30 minutes at or above the glass transition temperature, Tg, of the solid fluoropolymer, which for Telflon AF 1601® may be about 160 degrees C. The thickness of this layer may be about 10 microns to about 50 microns for some embodiments. This layer may then etched and over extruded with a water barrier layer such as PCTFE, braided and then overjacketed.

Figure 6:
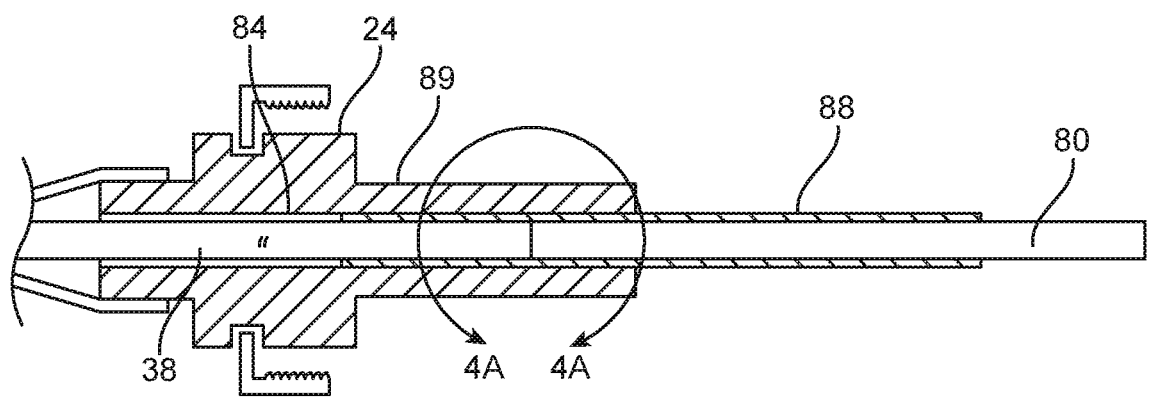
FIG. 6 is an enlarged elevation view in partial section of the laser connector ferrule embodiment of FIG. 3 for use with a liquid core ablation catheter.
Figure 7:
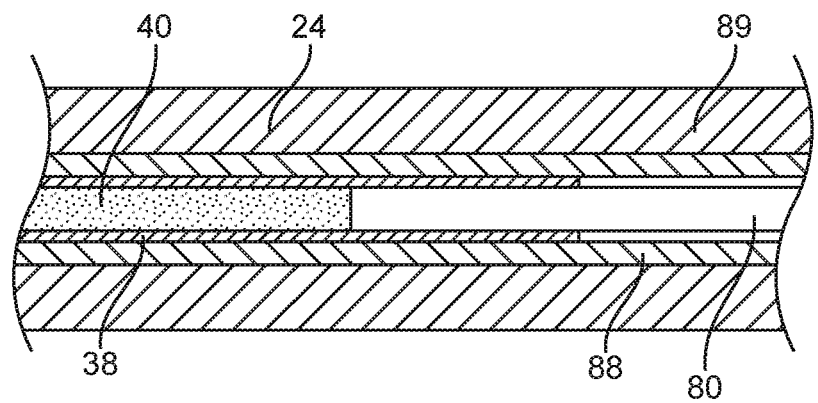
FIG. 7 is an enlarged view of the encircled portion 7 of the laser connector ferrule embodiment of FIG. 6.

The input window 80 and output window 82 enclosing the fluid volume 40 of the fluid core ablation catheter 22 generally include a material with a high transparency to the ultraviolet high power light pulses from the excimer laser or other suitable high power laser sources. The input optical window 80 as shown in FIG. 6 extends past the interface with the multi-layer catheter tube 38 in order that input laser energy spill over from an associated optical coupler 20 does not impinge on the multi-layer catheter tube 38 which could be heated and damaged. A tubular capillary shield 88 (see FIG. 6) may also be placed over the elongated cylindrical window 80 to further shield the catheter tube 38. The input optical window 80 may have a numerical aperture (NA) that is less than or matches the NA of the core fluid 40 of the ablation catheter 22 for optimum coupling in some cases. For some embodiments, the input optical window 80 may include a silica core silica clad window, but it may also include an optically polished silica rod that is radially surrounded by an air interface. The input optical window 80 of the ablation catheter 22 may also include a silica rod 90 (see FIG. 10) that has a low index amorphous fluoropolymer coating 91 such as Teflon AF 1601® or similar material applied to an outer surface thereof. For some embodiments, the input optical window 80 may have an outer diameter or transverse dimension of about 0.5 mm to about 1.5 mm, more specifically, about 0.8 mm to about 1.2 mm. The input window 80, capillary shield 88 and proximal end of the ablation catheter 22 are held in alignment and position for efficient coupling by a coupler body 89, as shown in FIG. 6, which includes a barrel member made from a high strength material with an inner lumen disposed therein. The proximal end of the ablation catheter 22 and distal end of the window 80 abut each other within the lumen of the barrel of the coupler body 89 as shown in FIG. 7. The capillary shield 88 may extend over the operative junction between the proximal end of the catheter tube 38 and distal end of the input window 80.

Figure 10:
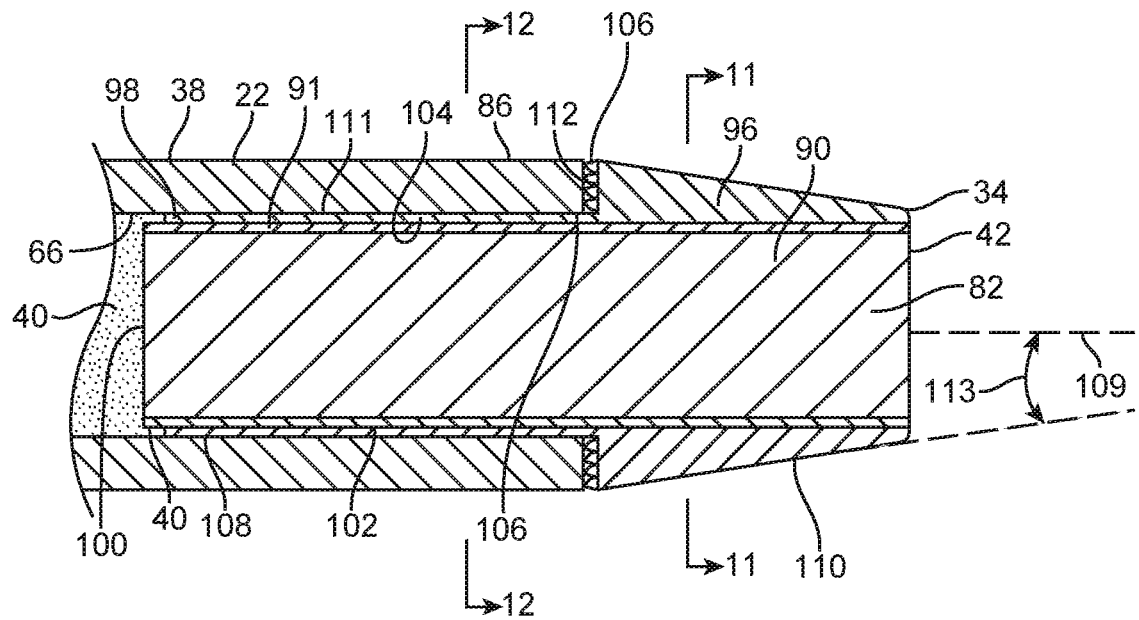
FIG. 10 is an elevation view in section of a distal portion of a liquid core ablation catheter embodiment including a tapered metal housing.
Figure 11:
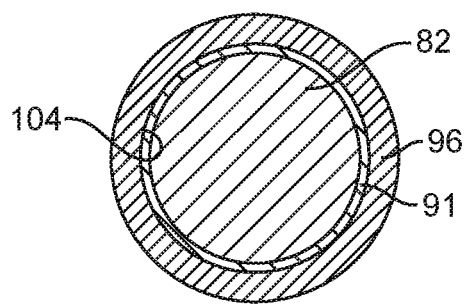
FIG. 11 is a transverse cross sectional view of the liquid core ablation catheter of FIG. 10 taken along lines 10-10 of FIG. 10.
Figure 12:
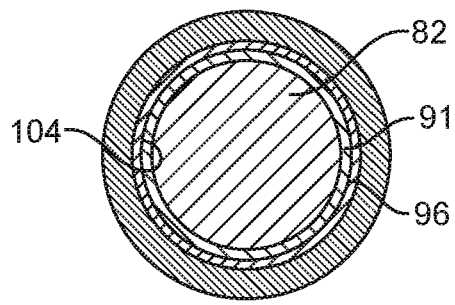
FIG. 12 is a transverse cross sectional view of the liquid core ablation catheter of FIG. 10 taken along lines 12-12 of FIG. 10.

The output optical window 82 as shown in FIG. 10 may have an overall length selected to minimize stiffness of the distal end 34 of the ablation catheter 22. In some cases, the output optical window 82 may have a length less than about 10 mm, more specifically, less than about 8 mm, even more specifically, less than about 6 mm, to allow the tip to negotiate curves in the body lumen. This output optical window 82 may have a numerical aperture equal to or greater than the numerical aperture of a tubular body portion of the liquid core ablation catheter 22 for maximum coupling of laser energy out of the liquid core 40. This output optical window 82 again may include a high NA optical fiber or a silica rod 90 coated with a low index amorphous fluoropolymer coating 91. For some embodiments, the output optical window 82 may have an outer diameter or transverse dimension of about 0.5 mm to about 1.5 mm, more specifically, about 0.8 mm to about 1.2 mm.

In order to protect the output optical window 82 from stresses and to ease passage of the fluid filled ablation catheter 22, a tapered metal housing 96 may be used to encapsulate the output optical window 82 as shown in the embodiment of FIG. 10. The output window 82 assembly at the distal end 34 of the ablation catheter 22 may be arranged with the proximal end 100 of the output optical window 82 extending proximally beyond a proximal end 98 of the tapered metal housing 96. The proximal end 100 of the output optical window 82 may extend proximally slightly into the core liquid 40 of the ablation catheter 22 in some cases as shown in FIG. 10. The tapered metal housing 96 may include an inner bore that extends the length of the tapered metal housing 96 from a proximal end to a distal end thereof. An inside surface 104 of the inner bore may be sized to fit closely with an outer surface 102 of the coating 91 of the output optical window 82 in some cases such that the output optical window 82 is stabilized laterally relative to the tapered housing but with enough gap to allow materials such as adhesives to extend therein. In some instances, the tapered metal housing 96 may be secured to the output optical window 82 by any suitable means such as by crimping, adhesive bonding, brazing, soldering or the like. In some cases, the tapered metal housing 96 may be so secured such that there may be little to no gap between the inside surface 104 of the inner bore of the tapered metal housing 96 and the outer surface 102 of the coating 91 output optical window 82. The tapered metal housing 96 may include a tapered distal section 110 that tapers down in outer diameter or dimension from a nominal outer diameter. The tapered distal section 110 may taper down to a reduced diameter or transverse dimension that may be up to about 0.012 inches larger than an outer transverse dimension or diameter of the output optical window 82. In some cases, the tapered distal section 110 may have a wall thickness at the distal end of the tapered distal section 110 of about 0.003 inches to about 0.005 inches. The tapered metal housing 96 may also include a stepped portion 111 that extends proximally from a proximal shoulder surface 112 of the tapered distal section 110. The stepped portion 111 may have a thin wall disposed between the inner bore and an outer surface 108 that has an outer transverse dimension or diameter that is small enough to be pushed into the inner lumen of the multi-layer catheter tube 38. In some cases, the wall thickness of the stepped portion 111 may be about 0.002 inches to about 0.006 inches, more specifically, about 0.003 inches to about 0.004 inches.

An outer surface 102 of the coating 91 of the output optical window 82 may be bonded to the inside surface 104 of the metal housing 96 with any suitable adhesive 106, such as a medical grade class VI adhesive. The inside surface 104 of the metal housing 96 may also be secured to the outer surface 102 of the output optical window 82 by any suitable method including crimping, adhesive bonding, soldering, brazing or the like depending on whether the window 82 is an all glass embodiment or polymer coated embodiment. The outer surface 108 of the stepped portion of the metal housing 96 may be secured to a surface such as an inner luminal surface 66 of the catheter tube 38 by bonding, such as adhesive bonding, or any other suitable method. The tapered distal section 110 of the metal housing 96 may provide for a more efficient cutting tip during the laser ablation process in that the configuration may provide for more active cutting area relative to the non-cutting area at the distal end of the ablation catheter embodiment 22. In addition, the tapered end 110 of the metal housing 96 may facilitate passage of the ablation catheter 22 through a lumen created by the laser ablation process. For some embodiments, an outer surface of the tapered end or section 110 may form an angle with respect to a longitudinal axis 109 of the ablation catheter 22 indicated by arrow 113. The angle 113 of the tapered end 110 of the metal housing 96 may be up to about 5 degrees in some cases, more specifically, about 1 degree to about 2 degrees, for some embodiments. In other embodiments, the angle 113 may be up to about 8 degrees, more specifically, about 6 degrees to about 8 degrees. Further, the metal housing 96 may provide mechanical support and strength to the output optical window 82 which may be made from brittle or relatively fragile materials, such as quartz, silica or the like. The tapered metal housing 96 may be made from a single piece of high strength metal such as stainless steel, NiTi, titanium or the like. Depending on the metal material of the tapered metal housing 96, the tapered metal housing 96 may be visible under fluoroscopic imaging and may be configured to serve as a radiopaque marker for the distal end of the liquid core ablation catheter 22. Other metals such as gold, tantalum, platinum or the like may also be included in the tapered metal housing 96 in order to facilitate radiopacity of the tapered metal housing 96.

Specific examples for use of the liquid core ablation catheter 22 are discussed herein that are directed to clearing obstructions in peripheral arteries of a patient, but similar approaches may be used for coronary arteries and other lumens 118 in the human body. To initiate a percutaneous procedure, a short introducing catheter (not shown) may be placed into an artery of the groin of a patient. All other devices may generally be introduced through this introducing catheter, which may include a hemostatic valve to eliminate blood flow out of the introducing catheter during the procedure. Contrast fluid may be introduced through this introducer sheath or a longer introducing catheter may be inserted through the sheath over a guide wire 56, as shown in FIG. 31, to locate this catheter near a target lesion 116 disposed within the patient's anatomy.

Figure 28:
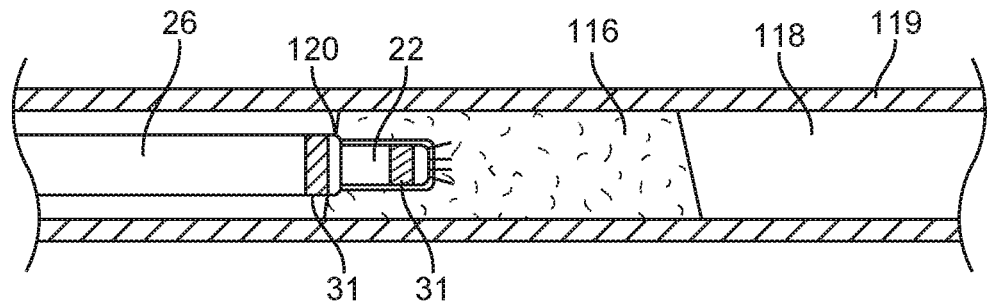
FIGS. 28 through 32 illustrate a method embodiment of a tissue ablation method.

In some cases, a method embodiment for using a liquid core ablation catheter system 22 may include placing the low profile support catheter 26 through the introducing sheath and advancing the support catheter 26 distally into close proximity to a target lesion or material 116 as shown in FIG. 28. In some instances, the support catheter 26 may be advanced, guided or positioned over a guidewire 56 during this process. If a guidewire 56 is used for advancing the support catheter 26, the guidewire 56 may then be removed once the distal end 120 of the support catheter 26 is disposed adjacent a target site or lesion 116. Once the guidewire 56 is removed from the inner lumen 28 of the support catheter 26, the liquid core ablation catheter 22 advanced distally within the inner lumen 28 of the support catheter 26 to the target lesion 116 as shown in FIG. 28. Saline may then be flushed through the inner lumen 28 of the support catheter 26 and around an outer surface of the liquid core ablation catheter 22 to remove blood from the tip of the ablation catheter 22. The laser source 10 may then be energized by depressing the footswitch 16 and laser energy at a level sufficient to ablate tissue then be emitted from the distal end 34 of the ablation catheter 22.

Figure 4:
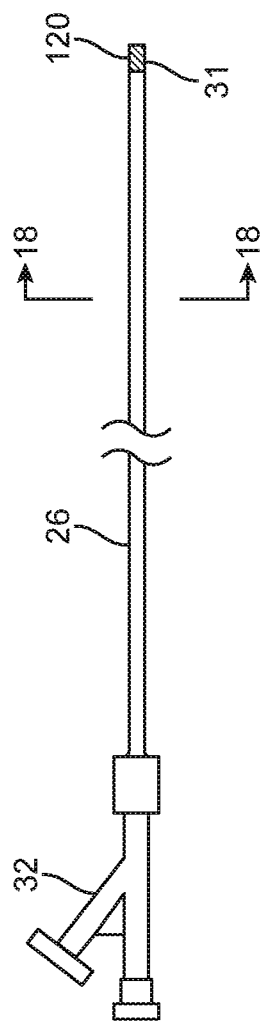
FIG. 4 is an elevation view of the support catheter embodiment of FIG. 2.
Figure 5:
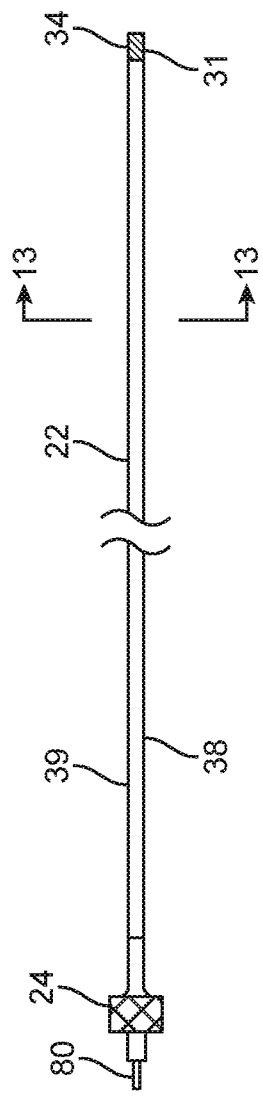
FIG. 5 is an elevation view of the liquid core ablation catheter embodiment of FIG. 2.
Figure 29:
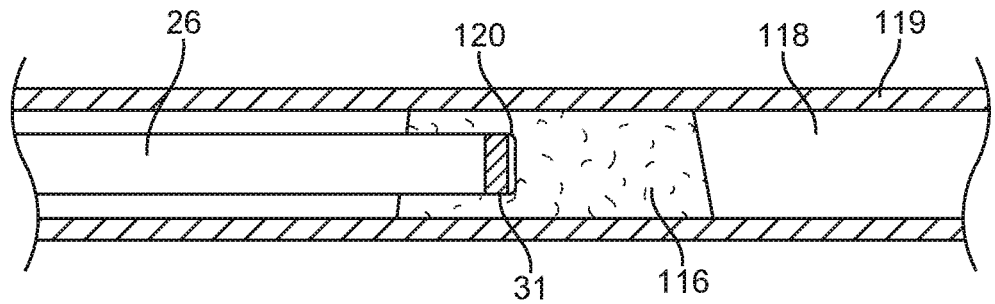
Figure 30:
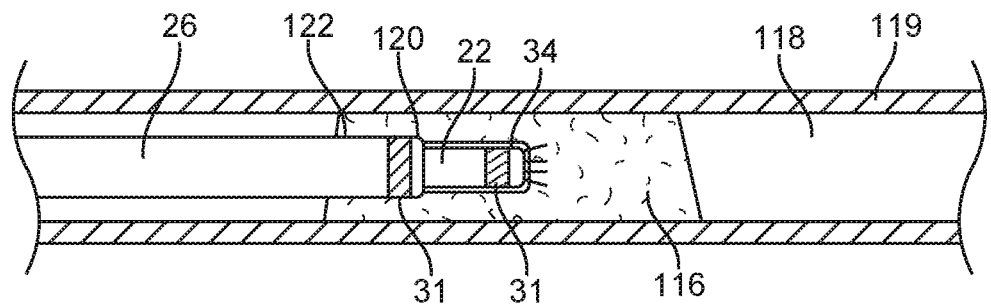
Figure 32:
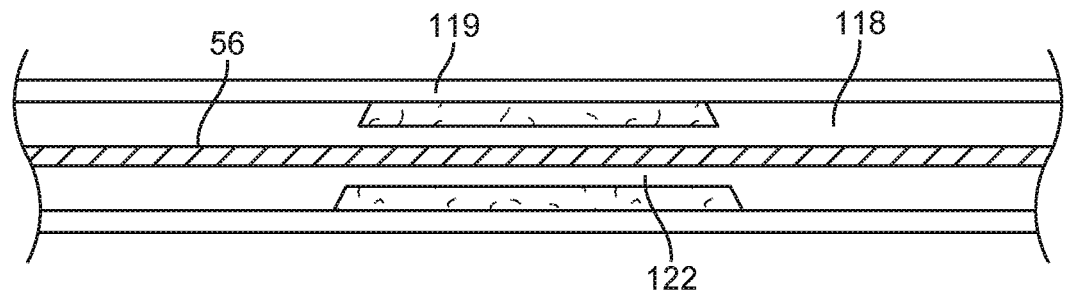

Upon activation of the laser, the distal end of the ablation catheter 22 may be advanced distally in an axial orientation into the target lesion 116 by a distance of about 5 to 10 mm for some embodiments, while the support catheter 26 remains substantially stationary with regard to its axial position. The support catheter 26 may then be advanced distally over the ablation catheter 22 and through the lumen 122 created by the active ablation catheter 22 until the distal tip 120, as shown in FIG. 4, of the support catheter 26 is substantially even with the distal tip 34 of the ablation catheter 22 as shown in FIG. 29. The relative positions of the respective distal ends 120 and 34 of the support catheter 26 and ablation catheter 22 may be determined by fluoroscopic imaging of the respective radiopaque marker bands 31 at the respective distal ends 120 and 34. The process is repeated as shown in FIG. 30 until the ablation catheter 22 crosses the lesion 116 as shown in FIG. 31. The ablation catheter 22 is removed with the support catheter 26 left in place and a guidewire 56 is advanced though the newly created channel or lumen 122. The support catheter 26 may then be retracted as shown in FIG. 32. Other devices, such as a balloon or a stent, may then be deployed over this guidewire 56 to achieve the necessary opening diameter in the vessel for adequate blood flow. If the laser catheter 22 produces a sufficient lumen 122, then no further treatment with additional devices is required in some instances.

For such a procedure, the support catheter 26 may be configured to have a low profile with thin walls to be able to follow the ablation catheter 22 through the lesion 116 and maintain the ablation end parallel to the lumen 122 to prevent perforation. To achieve this, the support catheter 26 may be a multilayer design with a thin wall liner 124 of a low friction Teflon®, such as polytetrafluoroethylene (PTFE) to allow passage of the ablation catheter with ease. An embodiment of the structure of a suitable support catheter is shown in FIG. 18.

Referring to FIG. 18, this liner 124 of the support catheter 26 may have an over layer or base layer tube 126 then a metal braid layer 128 disposed or braided over the base layer tube 126 to achieve pushability and kink resistance and torque. The base layer disposed over the PTFE liner 124 may have a high durometer with a very thin coating and an ideal material may include a polyimide base layer tube 126 covered with a thin over-jacket 130 of a lower durometer material for flexibility over the braid material layer 128. A wall thickness of the support catheter 26 of less than about 0.005" may be used for low profile for passage of the support catheter 26 through the opening or lumen 122 made by the liquid core ablation catheter 22. In essence this method may produce a result which is equivalent to a result achieved by using an external guidewire 56 for location of a cutting tip of an over-the-wire type design of the ablation catheter 22 as shown in FIGS. 15 and 16. The inner lumen 28 of the support catheter 26 may also include sufficient space or cross sectional area to accommodate both the ablation catheter 22 and a lumen or longitudinal space therebetween for flow of saline. A flow of saline or other desired fluid between an outside surface of the liquid core ablation catheter 22 and an inside surface of the inner lumen 28 of the support catheter 26 may be used to clear the blood which is disposed at the target lesion 116 site. In some cases, the saline may be introduced into the inner lumen 28 of the support catheter 26 with a syringe 19, as shown in FIG. 1, coupled to the Y connector 32 of the catheter system 27 as shown in FIGS. 1 and 2.

Some support catheter embodiments 26 may be straight as shown in FIG. 19 or have an angled tip as shown in the support catheter embodiment of FIG. 21 depending on the vessel contour at the lesion site. The support catheter 26 may have a low friction lubricious outer coating 132 on an outer surface 134 thereof (as shown in FIG. 18) for low friction passage though tissue follow the ablation catheter 22 through the lumen 122 created by the ablation catheter 22 through the target lesion 116. Visualization of the location of both the support catheter 26 and the ablation catheter 22 in the vessel lumen 118 and with respect to each other may be made by means of one or more radiopaque markers 31 or 136 disposed on the respective catheters at desired locations and with a least one marker located at each distal tip (120 and 34 respectively) of the catheters.

Interventional physicians often rely on a guidewire 56 for advancing multiple devices to treat a lesion 116 within a patient's vasculature and to maintain the position of a catheter inside the lumen walls. Some method embodiments discussed herein may include the use of a guidewire 56 to advance and/or position the support catheter 26. Once the support catheter 26 is properly positioned at a desired site within the patient's body, the guidewire 56 may then be removed and replaced with an ablation catheter such as the liquid core ablation catheter 22. Some interventionalist's may prefer the protection of a guidewire 56 to place other devices over in case of adverse event. In such cases, the ablation catheter 22 may be removed and a guidewire 56 inserted through the inner lumen 28 of the support catheter 26 and other treatment devices may then be passed over the guidewire 56 through the inner lumen 28 of the support catheter 26. In addition, the support catheter 26 may be removed before inserting other devices in some cases. One or more separate guidewire lumens 60 and 62 may also be attached to or integral with the support catheter 26 as shown on the support catheter embodiment 26''' of FIGS. 26 and 27. Additionally, a guidewire lumen may be added to the ablation catheter 22' as shown in FIGS. 15 and 16. In some cases, a separate guidewire lumen 60 or any of the guidewire lumens discussed herein may be suitable for passage of a 0.014" sized guidewire or the like may be used for additional protection. In some cases, this guidewire lumen would only have a short length at the distal end for a rapid exchange type configuration. This configuration could apply to the both the ablation catheter 22' and the support catheter 26'''. That way the physician would always have a guidewire present in case of an adverse event and has the ability to withdraw the liquid core ablation catheter 22 and advance a guidewire 56 over a total occlusion after the dense cap entrance to the total occlusion is cleared by energy emitted from the liquid core laser ablation catheter 22 as shown in FIG. 32. For some embodiments, the guidewire lumens 60 and 62 may have a length of at least about 10 cm. In addition, the respective distal ports of the guidewire lumens 60 and 62, which may be disposed along an outer surface of support catheter embodiments 26''', may be disposed proximally from a distal end of the support catheter 26''' by at least about 5 mm.

For some embodiments, a support catheter such as the support catheter 26''' may have multiple guidewire lumens 60 and 62 as shown in the embodiment of FIGS. 26 and 27, a support catheter such as the support catheter 26'' may have a tapered distal section as shown in the embodiment of FIG. 20, and the support catheter 26' may have a bend at the end as shown in the support catheter embodiment of FIG. 21 to negotiate bends in the artery or to displace the ablation catheter 22 towards an eccentric plaque. The multiple guidewire lumens 60 and 62 may be used for saline flush, contrast injection or for passage of a guidewire 56 in some cases.

Figure 33:
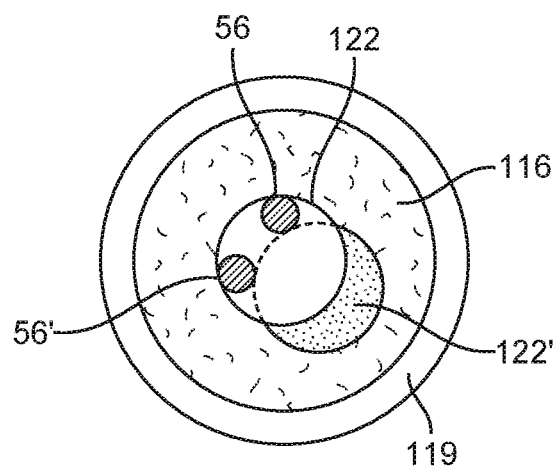
FIG. 33 is a transverse section view of a patient's vessel illustrating a method embodiment of producing a larger lumen after a first pass of an ablation catheter.
Figure 34:
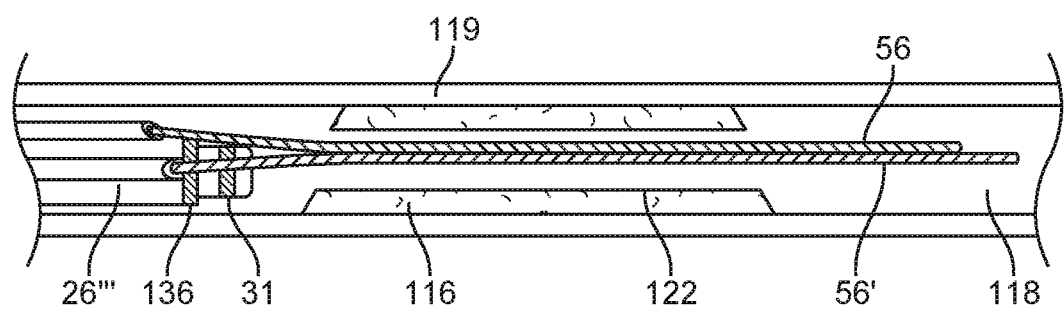
FIG. 34 is an elevation view in partial section of a patient's vessel lumen and catheter system embodiment disposed therein.
Figure 35:
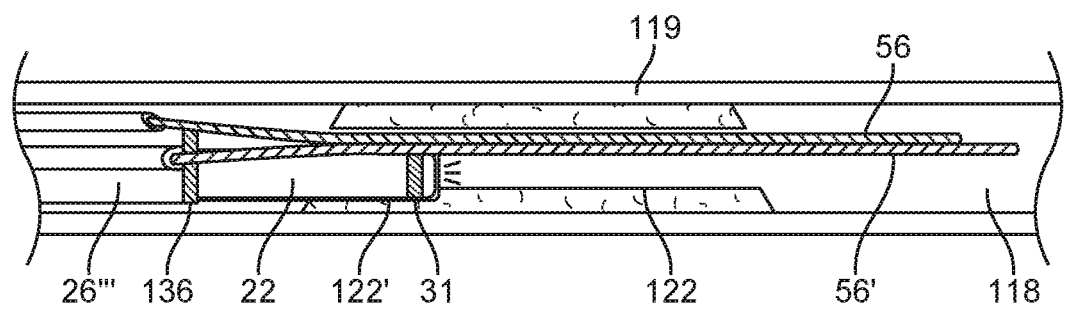
FIG. 35 is an elevation view in partial section illustrating an ablation catheter ablating new tissue laterally adjacent the pilot lumen.

For some indications, it may be desirable to make a channel in a patient's vessel lumen that is larger in transverse dimension than a transverse dimension of the ablation catheter 22 itself. For some such cases, after the liquid core ablation catheter 22, or any other suitable ablation catheter embodiment discussed herein, forms an initial channel and opens an occlusion 116 in a patient's vessel 118, a guidewire 56 or other device may then be inserted in the opening or newly formed channel 122. The ablation catheter 22 may then be activated to emit ablation energy and advanced through the initial channel 122 adjacent the substantially parallel guidewire 56 to produce a lumen 122' which is larger than the lumen made with the first active pass of the ablation catheter 22. Such a technique embodiment is shown in FIGS. 33-35. Embodiments of this procedure may be completed with a second guidewire 56' in a second guidewire lumen 60 or 62 of a support catheter embodiment 26''' and a final pass made. This method may produce a lumen 122' having a larger inner transverse dimension or diameter and corresponding larger transverse cross section than an outer transverse dimension or diameter or cross section of the ablation catheter 22 used to make the initial channel 122. During this type of method embodiment, the guidewire placements after the first or initial lumen is made block part of the initially created lumen which laterally forces the distal end of the liquid core ablation catheter 22 up against the remaining plaque 116. Such partial filling the first or initial channel with one, two, three or more guidewires 56 and 56' forces the ablation catheter 22 to ablate tissue disposed laterally with respect to the initial channel 122 formed by the ablation catheter 22. Without the guidewire placement in the initial channel 122, the ablation catheter 22 would likely just go through the first or initial lumen 122 on a second pass with no further ablation or channel widening or increase in cross sectional area. Such an increase in cross sectional area of the ablation channel allows more blood or other fluid to flow therethrough for a fixed pressure.

Figure 37:
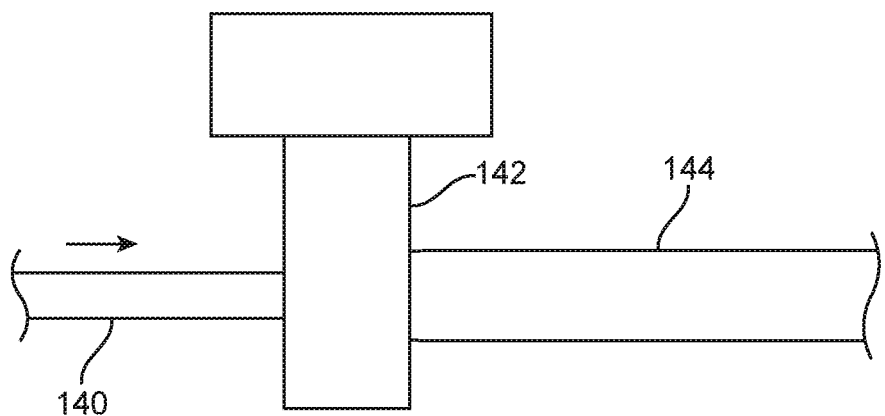
FIGS. 37-43 illustrate schematic representations of various catheter manufacturing process embodiments.
Figure 38:
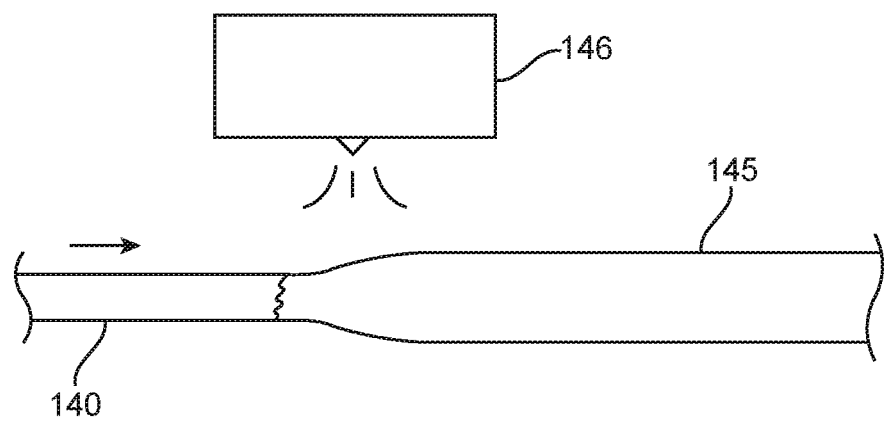
Figure 39:
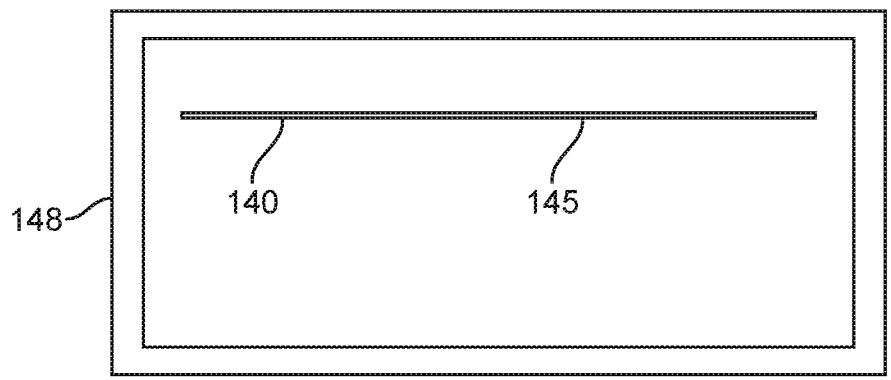
Figure 40:
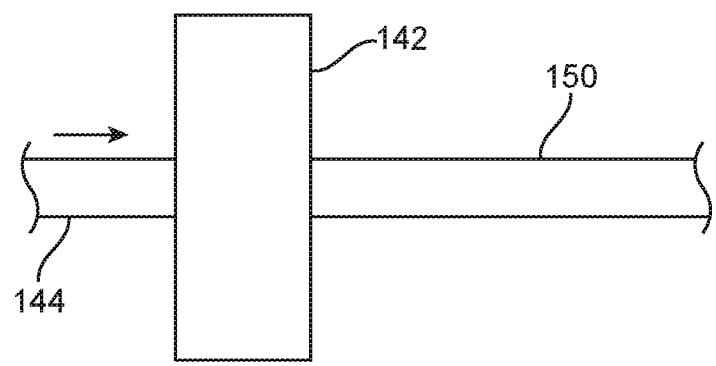
Figure 41:
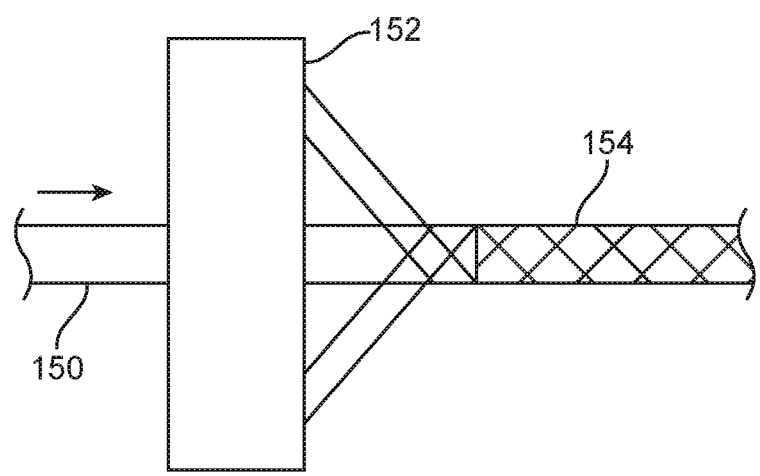
Figure 42:
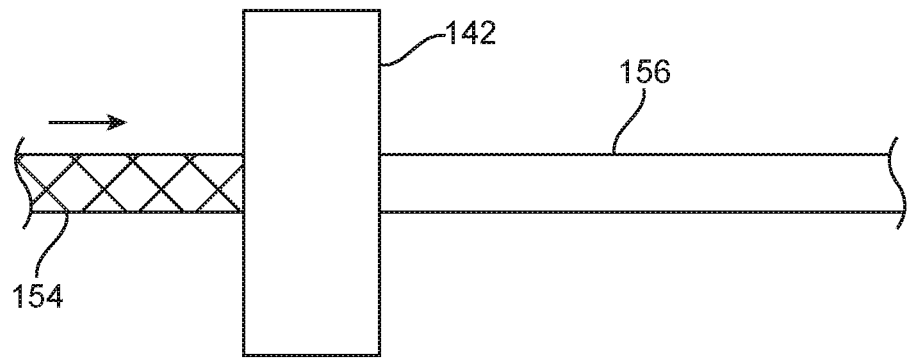
Figure 43:
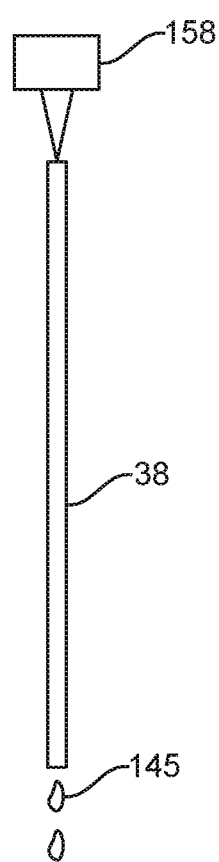

Referring to FIGS. 37-42, a variety of manufacturing steps are shown which may be useful for some or all of the processing method embodiments discussed above. In particular, FIG. 37 illustrates a polished metal mandrel 140 being passed through an extruder device 142 and applying a layer of amorphous fluoropolymer 144 to an outer surface of the mandrel 140. FIG. 38 shows a mandrel 140 having a solution of amorphous fluoropolymer 145 being applied to an outside surface of the mandrel 140 by a spray coating device 146 to produce a thin layer of amorphous fluoropolymer 144. FIG. 39 depicts a mandrel 140 with a coating of amorphous fluoropolymer solution 145 disposed in an oven 148 for thermal processing to drive off the solvent of the fluoropolymer solution 145. FIG. 40 shows a mandrel 140 with a layer of amorphous fluoropolymer 144 applied thereto being passed through an extruder 142 to apply a layer of base tube material 150. FIG. 41 shows the mandrel 140 of FIG. 40 with a layer of amorphous fluoropolymer 144 and subsequent base layer tube material 150 being passed through a braiding device 152 to apply a braided layer 154 to the base tube layer 150. FIG. 42 shows the mandrel 140 and layers 144, 150 and 154 being passed through an extruder 142 to apply an outer jacket layer 156. FIG. 43 shows an amorphous fluoropolymer solution 145 being injected into a catheter tube 38 by a pressurized amorphous solution source 158 which may be further processed to remove the solvent from the solution 145 in an oven 148 as shown in FIG. 39.

Figure 44:
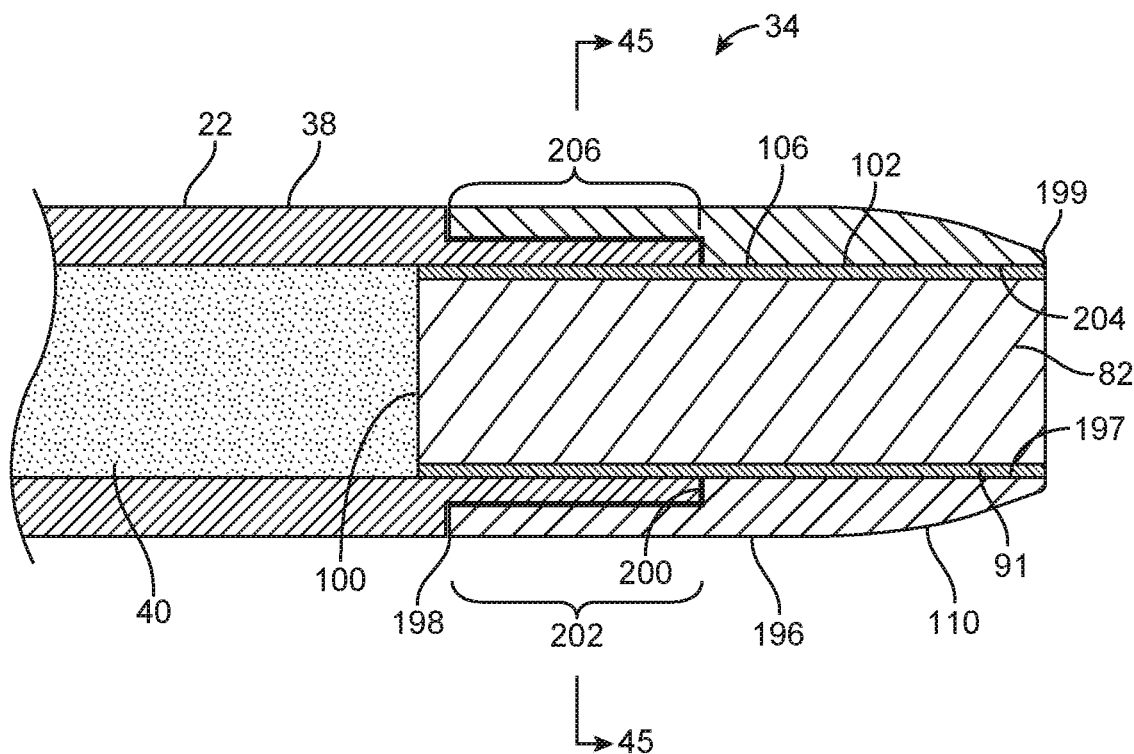
FIG. 44 is an elevation view in section of a distal portion of a liquid core ablation catheter embodiment including a tapered metal housing.
Figure 45:
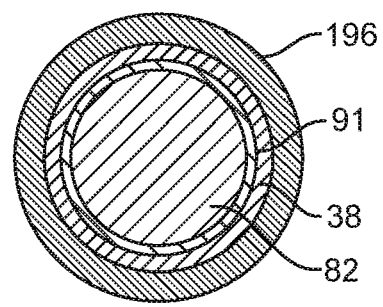
FIG. 45 is a transverse cross section view of the liquid core ablation catheter of FIG. 44 taken along lines 45-45 of FIG. 44.

FIG. 44 shows a distal portion of an embodiment of a liquid core ablation catheter that may have some or all of the properties of liquid core ablation catheter 22 discussed above. Once again, in order to protect the output optical window 82 from stresses and to ease passage of the fluid filled ablation catheter 22 through tissue during ablation, a tapered metal housing 196 may be used to encapsulate the output optical window 82 as shown in the embodiment of FIG. 44. The output window 82 assembly at the distal end 34 of the ablation catheter 22 may be arranged with the proximal end 100 of the output optical window 82 extending proximally beyond a proximal end 198 of the tapered metal housing 196.

The proximal end 100 of the output optical window 82 may extend proximally slightly into the core liquid 40 of the ablation catheter 22 in some cases as shown in FIG. 44. The tapered metal housing 196 may include an inner bore 197 that extends the length of the tapered metal housing 196 in a proximal direction from a distal end 199 of the housing 196 to a distal end 200 of a stepped portion 202 of the housing 196. An inside surface 204 of the inner bore may be sized to fit closely with an outer surface 102 of the coating 91 of the output optical window 82 in some cases such that the output optical window 82 is stabilized laterally relative to the tapered housing but with enough gap to allow materials such as adhesives to extend therein. In some instances, the tapered metal housing 196 may be secured to the output optical window 82 by methods such as by crimping, adhesive bonding, soldering, brazing or the like. In some cases the tapered metal housing 196 may be secured such that there may be little to no gap between the inside surface 204 of the bore 197 of the tapered metal housing 196 and the outer surface 102 of the coating 91 of the output optical window 82. The tapered metal housing 196 may include a tapered distal section 110 that tapers down in outer diameter or dimension from a nominal outer diameter. The tapered distal section 110 may taper down to a reduced diameter or transverse dimension that may be up to about 0.012 inches larger than an outer transverse dimension or diameter of the output optical window 82, in some cases up to about 0.010 inches larger. In some cases, the tapered distal section 110 may have a wall thickness at the distal end 199 of the tapered distal section 110 of about 0.003 inches to about 0.005 inches. The stepped portion 202 of the housing 196 may have a thin wall disposed over a reduced diameter portion 206 of a distal section of the multilayer catheter tube 38. In some cases, the stepped portion 202 of the tapered metal housing 196 may have the same or similar longitudinal length as that of the reduced diameter portion 206 of the distal section of the multilayer catheter tube 38. In some cases, the wall thickness of the stepped portion 202 may be about 0.002 inches to about 0.005 inches, more specifically, about 0.003 inches to about 0.004 inches. In some cases, the wall thickness of the reduced diameter portion 206 of the multilayer catheter tube 38 may be sized to have an overall outer diameter to substantially match an inside diameter or transverse dimension of the stepped portion 202 of the tapered metal housing 196. In addition, the inside surface of the stepped portion 202 may be secured to an outer surface of the reduced diameter portion 206 with an adhesive bond, crimp connection or the like. In some instances, it may be desirable for an outside diameter or transverse dimension of the tapered metal housing 196 to be the same as or substantially the same as an outside diameter or transverse dimension of the nominal multilumen catheter tube 38 so as to provide a smooth regular transition between an outside surface of the tapered metal housing 196 and an outside surface of the multilumen catheter tubing 38.

The outer surface 102 of the output optical window 82 may be bonded to an inside surface 204 of the metal housing 196 with any suitable adhesive 106, such as a medical grade class VI adhesive or the like. For all glass embodiments of the output optical window 82, methods such as soldering or bronzing may be used. The inside surface 204 of the bore 197 of the metal housing 196 may also be mechanically secured to the outer surface 102 of the output optical window 82 by methods such as crimping or any other suitable mechanical method as discussed herein. As discussed above, the tapered distal section 110 of the metal housing 196 may provide for a more efficient cutting tip during the laser ablation process in that the configuration may provide for more active cutting area relative to the non-cutting area at the distal end of the ablation catheter embodiment 22. In addition, the tapered end 110 of the metal housing 196 may facilitate passage of the ablation catheter 22 through a lumen created by the laser ablation process. For some embodiments, the tapered end 110 of the tapered metal housing 196 may have the same or similar configuration as that of tapered metal housing 96 discussed above and as shown in FIGS. 10-12. In particular, the tapered end 110 may form an angle 113 with respect to a longitudinal axis 109 of the ablation catheter 22 indicated by arrow 113 in FIG. 10 of up to about 5 degrees in some cases, more specifically, about 1 degree to about 2 degrees, for some embodiments. In some instances, the tapered end 110 of the tapered metal housing 96, or any other tapered metal housing embodiment discussed herein, may form an angle 113 of up to about 9 degrees, more specifically, of about 6 degrees to about 8 degrees. Further, the metal housing 196 may provide mechanical support and strength to the output optical window 82 which may be made from brittle or relatively fragile materials, such as quartz, silica or the like. The tapered metal housing 196 may be made from a single piece of high strength metal such as stainless steel, titanium or the like. Depending on the metal material of the tapered metal housing 196, the tapered metal housing 196 may be visible under fluoroscopic imaging and may be configured to serve as a radiopaque marker for the distal end of the liquid core ablation catheter 22. Other metals such as gold, tantalum, platinum or the like may also be included in the tapered metal housing 196 in order to facilitate radiopacity of the tapered metal housing 196.

FIGS. 46-50 illustrate an embodiment of a high energy laser coupler 220 that may be operatively coupled to a proximal end of any of the liquid core ablation catheters embodiments 22 discussed herein as well as any other suitable laser ablation catheter. For some embodiments, the high energy laser coupler 220 may include a coupler body 222 that has a proximal section 224 with a cylindrical outer surface 226 and an inner bore 228 which is disposed concentrically within the cylindrical outer surface 226. The inner bore 228 extends distally from a proximal end 230 of the coupler body 222 to a proximal end 232 of a window connector bore 234. The window connector bore 234 is disposed at a distal end of the inner bore 228. The coupler body 222 also includes a distal section 236 extending distally from the window connector bore 234.

A window connector body 240 includes a proximal section 241 with a cylindrical outer surface which may be configured to fit closely within an inside surface of the window connector bore 234 of the coupler body 222. A flange portion 244 of the window connector body 240 is disposed at a distal portion or distal end of the proximal section 241 and extends radially outward from a nominal outer surface 246 of the proximal section 241 of the window connector body 240. The window connector body 240 also includes a stepped portion 250 which extends distally from the proximal portion and has an outer diameter or transverse dimension that is less than an outer diameter or transverse dimension of the proximal section 241 of the window connector body 240. The outer diameter of the stepped portion 250 may be configured to extend within an inner lumen of a proximal section of the multilayer catheter tube 38. An outer surface 252 of the stepped portion 250 may be secured to an inside surface of the proximal section of the multilayer catheter tube 38 by an adhesive bond, crimp bond or the like. An inner bore 254 extends the length of the window connector body 240 from a proximal end 242 to a distal end 245 thereof. The inner bore 254 may be a straight bore that is configured to fit closely with an outer surface 256 of an optical input window 80 disposed within and secured to the inner bore 254 of the window connector body 240. The outer surface 256 of the optical input window 80 may be secured to an inside surface of the inner bore 254 of the window connector body 240 with an adhesive bond, crimp bond, solder bond, braze bond or the like. In some cases, it may be desirable for the bond between the outer surface 256 of the input optical window 80 and the inside surface of the bore 254 of the window connector body 240 to be fluid tight.

Figure 49:
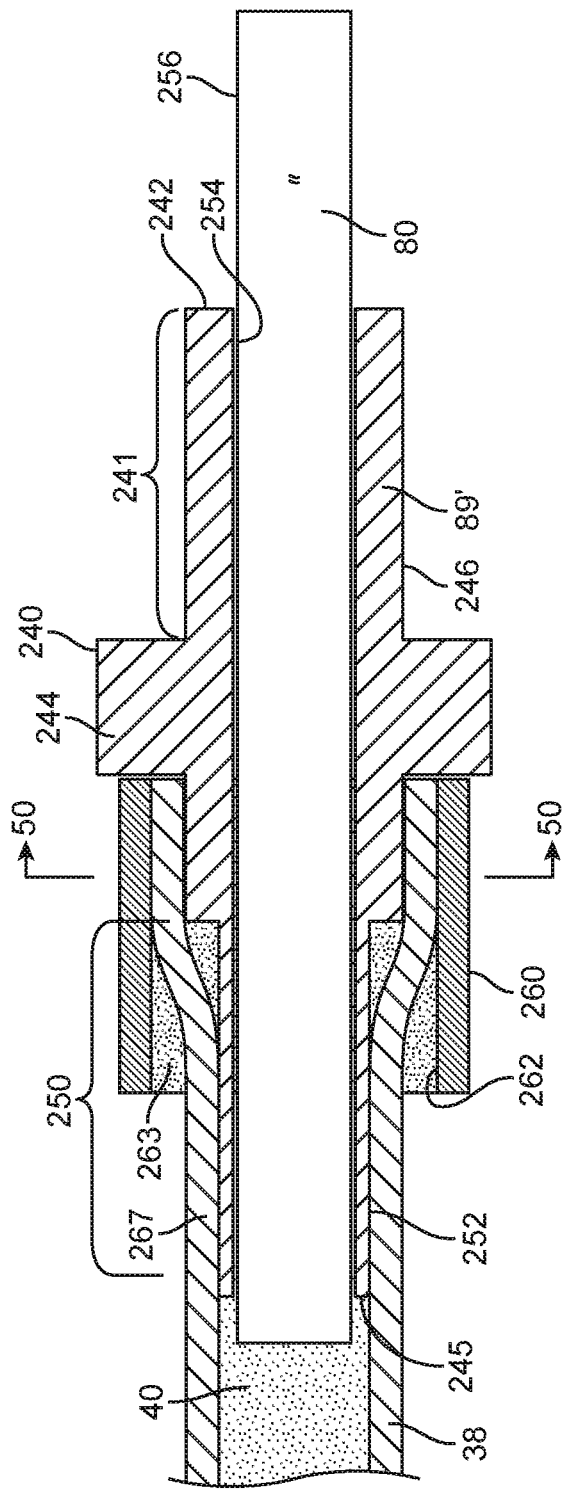
FIG. 49 is an enlarged view of the encircled portion 49 of the laser connector ferrule embodiment of FIG. 46.
Figure 50:
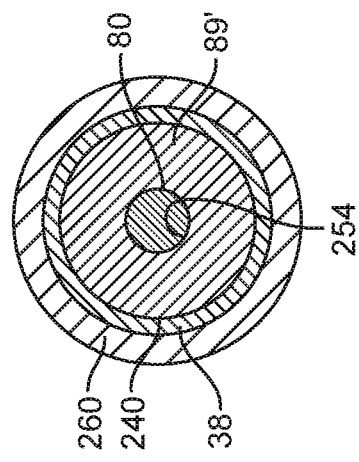
FIG. 50 is a transverse cross section view of the input optic coupler assembly of the laser coupler of FIG. 49 taken along lines 50-50 of FIG. 49.

In some instances, a proximal end of the optical input window 80 may extend proximally from a proximal end 242 of the proximal section 241 of the window connector body 240. As shown in FIGS. 49 and 50, a proximal portion of the flexible waveguide catheter tube 38 is disposed over the stepped portion 250 of the window connector body 240 with a cylindrical metal sleeve 260 disposed over the proximal portion of the flexible waveguide catheter tube 38. The cylindrical metal sleeve 260 may be disposed so at to secure an inside surface of the catheter tube 38 to an outside surface of the stepped portion 250 of the window connector body 240 in a fluid tight seal. The inside surface of the multilayer catheter tube 38 may be secured to an outside surface of the stepped portion 250 with an adhesive bond 263. In some cases, an inside surface 262 of the metal sleeve 260 may be secured to an outside surface of a proximal portion 267 of the multilayer catheter tube 38 with an adhesive bond 263, with a crimp body or the like. In addition, a potting material 264 such as an adhesive or the like may be used to provide mechanical support and strain relief between an outer surface of the multilayer catheter tube 38 and an inside surface of a back bore 266 of the distal section of the coupler body 222.

The optical input window 80, which may include a multi-mode length of optical fiber in some instances. In some embodiments, the optical input window 80 may extend distally of a distal end 245 of the stepped portion of the window connector body 240 making direct contact with liquid core fluid 40 of the liquid core ablation catheter. In some instances, the optical input window may have axial length of about 0.5 inches to about 1 inch. For some embodiments, the stepped portion of the window connector body may have a wall thickness of about 0.002 inches to about 0.004 inches.

Figure 51:
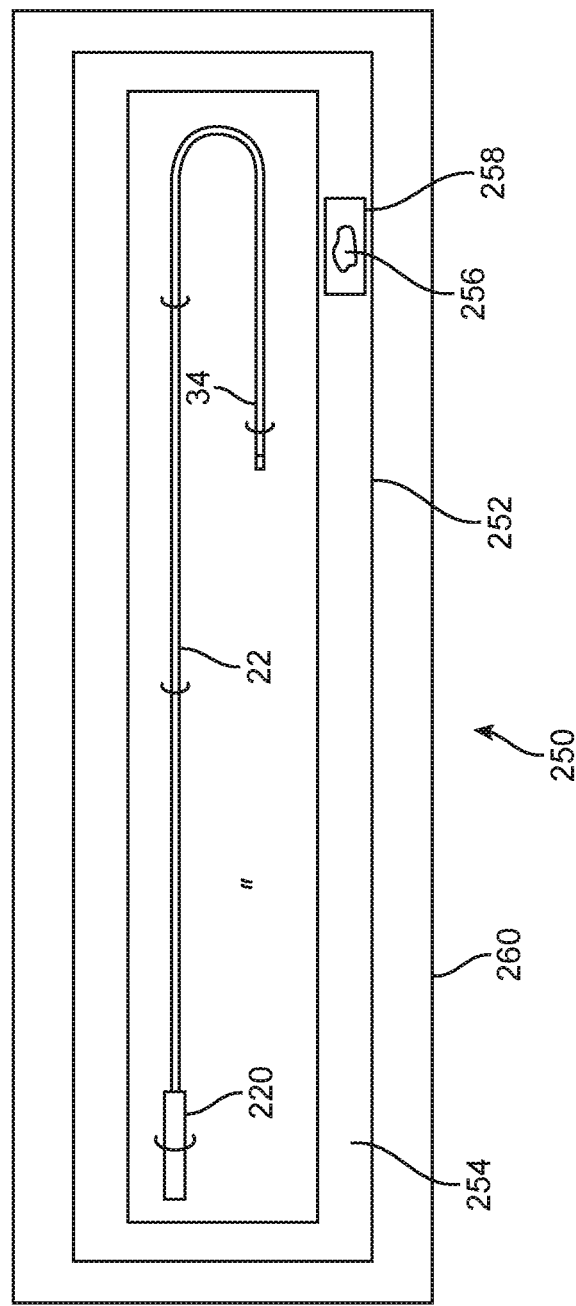
FIG. 51 shows a schematic representation of a packaging embodiment for use with a liquid core ablation catheter.

Regard packaging and transportation of liquid core ablation catheter embodiments discussed herein, certain conditions or structures may be desirable in order to keep the catheter embodiments in good working order. In some cases, it may be important to maintain a minimum vapor pressure of liquid in the environment surrounding some liquid core ablation catheter embodiments 22 in order to prevent loss of core fluid 40 during storage or transportation of the catheter 22 due to diffusion through the catheter tube 38. It may also be important to minimize temperature extremes to which some liquid core ablation catheter embodiments are exposed. FIG. 51 shows a liquid core ablation catheter package assembly 250 that includes a thin walled hermetically sealed enclosure 252 including an interior volume 254. In some cases, a material of the enclosure 252 may be suitable for gamma sterilization. A liquid core ablation catheter 22 is shown disposed within the interior volume 254 of the hermetically sealed enclosure 252, however, any suitable liquid core ablation catheter discussed herein may be so packaged. A liquid 256 is disposed within the interior volume and is configured to maintain a vapor pressure within the interior volume 254 sufficient to prevent loss of a liquid 40 of a liquid core 40 of the liquid core ablation catheter 22 due to diffusion of the liquid core 40 into the interior volume 254. The hermetic properties of the enclosure 252 prevents the liquid 256 from escaping the enclosure 252, thus only a small amount of the liquid 256 may be necessary. In some instances, the thin walled hermetically sealed enclosure may be made from a thin metalized plastic or a non-metalized thin plastic such as PCTFE that functions as a suitable liquid vapor barrier. The thin walled plastic may include heat sealed edges in order to form the enclosure from two flat thin sheets of the plastic material. The package assembly may also include a liquid depot 258 that contains the liquid 256 disposed within the interior volume 254. In some cases, the liquid depot 258 may include a sponge or the like that may also be configured to absorb a liquid such as the core liquid 40 and be suitable for gamma sterilization. In addition, the sealed enclosure 252 may be disposed within a substantially rigid box 260.

With regard to the above detailed description, like reference numerals used therein may refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

The entirety of each patent, patent application, publication and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" may refer to one of or a plurality of the elements it modifies (e.g., "a reagent" can mean one or more reagents) unless it is contextually clear either one of the elements or more than one of the elements is described. Although the present technology has been specifically disclosed by representative embodiments and optional features, modification and variation of the concepts herein disclosed may be made, and such modifications and variations may be considered within the scope of this technology.

Certain embodiments of the technology are set forth in the claim(s) that follow(s).

What is claimed is:

1. A support catheter for use supporting a liquid core ablation catheter, comprising:
   an inner tubular layer comprising a thin wall liner comprising a low friction material, a base layer of high durometer material disposed over the thin wall liner and an inner lumen with an inner diameter which is configured to accommodate passage of the liquid core ablation catheter;
   a braided layer disposed over an outer surface of the inner tubular layer;
   an outer layer covering the braided layer;
   a total wall thickness of 0.005 inches or less; and
   a torqueability, pushability and kink resistance sufficient to guide the liquid core ablation catheter with a low enough profile to advance through an opening generated by laser ablation of tissue with the liquid core ablation catheter.

2. The support catheter of claim 1 wherein the low friction material of the inner tubular layer comprises PTFE, a hybrid of PTFE or other low friction polymer suitable for sterilization.

3. The support catheter of claim 1 further comprising at least one radiopaque marker disposed near a distal end of the support catheter to visualize the position of the distal end of the support catheter in a patient's body lumen and a position of the support catheter with respect to the liquid core ablation catheter disposed within the support catheter.

4. The support catheter of claim 1 wherein a distal section of the support catheter comprises a straight longitudinal section.

5. The support catheter of claim 1 further comprising an angled distal section configured for proper positioning of a distal end of the liquid core ablation catheter disposed within the inner lumen of the inner tubular layer of the support catheter.

6. The support catheter of claim 1 further comprising an angled distal section configured to nutate a distal end of the liquid core ablation catheter disposed within and extending distally from the support catheter upon rotation of the support catheter about a longitudinal axis thereof.

7. The support catheter of claim 6 wherein the angled distal section has a length of 5 mm to 50 mm.

8. The support catheter of claim 6 wherein a discharge axis of the angled distal section forms an angle of 3 degrees to 10 degrees with respect to a longitudinal axis of the support catheter.

9. The support catheter of claim 1 wherein a distal section of the support catheter comprises a tapered distal section configured to align a distal end of the liquid core ablation catheter which is disposed within the inner lumen of the inner tubular layer of the support catheter away from a wall of a patient's body lumen.

10. The support catheter of claim 1 wherein the low friction material of the thin wall liner comprises polytetrafluoroethylene and the high durometer material of the base layer comprises polyimide.

11. The support catheter of claim 1 wherein the inner diameter of the inner lumen of the inner tubular layer is configured to accommodate passage of the liquid core ablation catheter with space therebetween sufficient for saline injection to flush blood and contrast fluid distal of the liquid core ablation catheter distal end.

12. A catheter system, comprising:
    a liquid core ablation catheter having an outer diameter of 1 mm to 2.5 mm; and
    a support catheter for use supporting the liquid core ablation catheter, the support catheter comprising:
      an inner tubular layer comprising a thin wall liner comprising a low friction material, a base layer of high durometer material disposed over the thin wall liner and an inner lumen with an inner diameter which is configured to accommodate passage of the liquid core ablation catheter,
      a braided layer disposed over an outer surface of the inner tubular layer,
      an outer layer covering the braided layer,
      a total wall thickness of 0.005 inches or less, and
      a torqueability, pushability and kink resistance sufficient to guide the liquid core ablation catheter with a low enough profile to advance through an opening generated by laser ablation of tissue with the liquid core ablation catheter.

13. The support catheter of claim 1 wherein the low friction material of the thin wall liner comprises polytetrafluoroethylene and the high durometer material of the base layer comprises polyimide.

14. The catheter system of claim 12 wherein the inner diameter of the inner lumen of the inner tubular layer is configured to accommodate passage of the liquid core ablation catheter with space therebetween sufficient for saline injection to flush blood and contrast fluid distal of the liquid core ablation catheter distal end.

* * * * *